US006962820B2

(12) United States Patent
Bell et al.

(10) Patent No.: US 6,962,820 B2
(45) Date of Patent: Nov. 8, 2005

(54) ANALYTE DETECTION SYSTEM

(75) Inventors: Michael L. Bell, Fullerton, CA (US); Yuan Lin, Walnut, CA (US); Josephine M. Michael, Placentia, CA (US); Stephen L. Pentoney, Jr., Chino Hills, CA (US); Tsong-Tseh Tsay, Hsin Chu (TW)

(73) Assignee: Beckman Coulter, Inc., Fullerton, CA (US)

( * ) Notice: Subject to any disclaimer, the term of this patent is extended or adjusted under 35 U.S.C. 154(b) by 50 days.

(21) Appl. No.: 10/779,357

(22) Filed: Feb. 12, 2004

(65) Prior Publication Data

US 2004/0166595 A1 Aug. 26, 2004

Related U.S. Application Data

(62) Division of application No. 09/990,678, filed on Nov. 14, 2001, now Pat. No. 6,838,289.

(51) Int. Cl.⁷ .............................................. G01N 21/64
(52) U.S. Cl. ................. 436/172; 422/82.07; 422/82.08; 250/458.1; 250/459.1
(58) Field of Search .............................. 536/26.1, 18.7, 536/22.1; 436/172, 523, 546; 422/82.07, 82.08; 250/458.1, 459.1

(56) References Cited

U.S. PATENT DOCUMENTS

| | | | |
|---|---|---|---|
| 2,887,479 A | 5/1959 | Heseltine | |
| 2,895,955 A | 7/1959 | Heseltine et al. | |
| 4,256,834 A * | 3/1981 | Zuk et al. .................. | 435/7.72 |
| 4,318,707 A * | 3/1982 | Litman et al. .............. | 436/537 |
| 4,325,706 A | 4/1982 | Gershman et al. | |
| 4,499,052 A | 2/1985 | Fulwyler | |
| 4,609,689 A * | 9/1986 | Schwartz et al. ........... | 523/202 |
| 4,661,913 A | 4/1987 | Wu et al. | |
| 4,719,182 A * | 1/1988 | Burdick et al. ............. | 436/501 |
| 4,729,947 A | 3/1988 | Middendorf et al. | |
| 4,745,285 A | 5/1988 | Recktenwald et al. | |
| 4,772,561 A | 9/1988 | Genshaw .................... | 436/169 |
| 4,839,265 A | 6/1989 | Ohno et al. | |
| 4,882,265 A | 11/1989 | Laganis et al. | |
| 4,933,269 A | 6/1990 | Parton et al. | |
| 4,973,572 A | 11/1990 | DeBoer | |
| 5,028,545 A | 7/1991 | Soini | |
| 5,037,734 A | 8/1991 | Lenhard et al. | |
| 5,061,618 A | 10/1991 | Parton et al. | |
| 5,162,863 A | 11/1992 | Ito | |
| 5,207,880 A | 5/1993 | Middendorf et al. | |
| 5,219,763 A | 6/1993 | Van Hoegaerden ......... | 436/523 |
| 5,268,486 A | 12/1993 | Waggoner et al. | |
| 5,312,921 A | 5/1994 | Glazer et al. | |
| 5,321,130 A | 6/1994 | Yue et al. | |
| 5,340,422 A | 8/1994 | Chang et al. ................. | 156/89 |
| 5,366,603 A | 11/1994 | Middendorf et al. | |
| 5,375,606 A | 12/1994 | Slezak et al. | |
| 5,405,784 A | 4/1995 | Van Hoegaerden ......... | 436/523 |
| 5,410,030 A | 4/1995 | Yue et al. | |
| 5,556,959 A | 9/1996 | Brush et al. | |
| 5,571,388 A | 11/1996 | Patonay et al. | |
| 5,573,909 A | 11/1996 | Singer et al. .................. | 435/6 |
| 5,585,241 A | 12/1996 | Lindmo | |
| 5,627,040 A | 5/1997 | Bierre et al. | |
| 5,682,038 A | 10/1997 | Hoffman | |
| 5,736,330 A | 4/1998 | Fulton | |
| 5,747,349 A | 5/1998 | van den Engh et al. | |
| 5,763,189 A * | 6/1998 | Buechler et al. ............. | 435/7.1 |
| 5,808,044 A | 9/1998 | Brush et al. | |

(Continued)

FOREIGN PATENT DOCUMENTS

| | | |
|---|---|---|
| EP | 0609894 | 8/1994 |
| EP | 0 753 584 | 7/1996 |
| EP | 0 670 374 | 5/1998 |
| WO | WO 99/19515 | 4/1999 |
| WO | WO 99/37814 | 7/1999 |

OTHER PUBLICATIONS

Strekowski, Lucjan, *Substitution Reactions of a Nucleofugal Group in Heptamethine Cyanine Dyes. Synthesis of an Isothiocyanota Derivative for Labeling of Proteins with a Near–Infrared Chromophore*, J. Org. Chem. 57, 4578–4580 (1992).

Slominskii, Y.L., *Polymethine Dyes with Hydrocarbon Bridges, Enamino Ketones in the Chemistry of Cyanine Dyes*, Journal of Organic Chemistry of the USSR, vol. 19, No. 10, pp. 2134–2142 (1983).

Strekowski, Lucjan, *Facile Derivations of Heptamethine Cyanine Dyes*, Synthetic Communications, 22(17), 2593–2598 (1992).

Slominskii, Y.L., *Tricarbocyanines with Hydrogen Rings in the Chromophore*, Journal of Organic Chemistry of the USSR, vol. 40, No. 6, pp. 625–628 (1974).

Arnold, Z., *Synthetic Reactions of Dimethylformamide, XXII. Formation and Preparation of Formyl Derivatives of Indene*, Collection Czechoslov. Chem. Commun., vol. 30, 2783–2792 (1965).

(Continued)

Primary Examiner—Jeffrey R. Snay
(74) Attorney, Agent, or Firm—Sheldon & Mak; Jeffrey G. Sheldon; Kristin C. Hübner

(57) ABSTRACT

An analyte detection system utilizing a combination of fluorescent labels for labeling particles and an analyte specific fluorescent analyte detection dye. The particles contain a combination of fluorescent labels for coding the particles and an analyte specific fluorescent dye. The particles can be used to identify and quantify analytes in an analytical sample by reaction of the analytical sample with the particles. An analytical device can identify the particles according to the combination of fluorescent labels. The device can then correlate the identified particle with the analyte specific fluorescent analyte detection dye. Multiple subpopulations of particles can be used to identify and quantify multi-analytes in a single analytical sample. Near infrared (NIR) fluorescent labels useful in the detection system are also provided.

24 Claims, 13 Drawing Sheets

U.S. PATENT DOCUMENTS

| | | | |
|---|---|---|---|
| 5,880,474 | A | 3/1999 | Norton et al. |
| 5,981,180 | A | 11/1999 | Chandler et al. ............... 435/6 |
| 5,986,086 | A | 11/1999 | Brush et al. |
| 6,027,709 | A | 2/2000 | Little et al. ................. 424/1.65 |
| 6,028,190 | A | 2/2000 | Mathies et al. ............ 536/26.6 |
| 6,048,982 | A | 4/2000 | Waggoner |
| 6,074,609 | A | 6/2000 | Gavin et al. ................... 422/99 |
| 6,130,094 | A | 10/2000 | Waggoner et al. ............ 436/63 |
| 6,159,748 | A | 12/2000 | Hechinger |
| 6,406,667 | B1 * | 6/2002 | Singh et al. ................... 422/52 |
| 6,449,562 | B1 | 9/2002 | Chandler et al. ............. 702/19 |
| 6,455,263 | B2 | 9/2002 | Payan ........................ 435/7.1 |
| 6,524,793 | B1 | 2/2003 | Chandler et al. .............. 435/6 |
| 6,630,307 | B2 | 10/2003 | Bruchez et al. ................. 435/6 |
| 6,682,940 | B2 | 1/2004 | Pankowsky ................. 436/176 |
| 6,778,910 | B1 | 8/2004 | Vidal et al. .................... 702/21 |
| 6,797,481 | B1 | 9/2004 | Ullman et al. ............... 435/7.1 |
| 6,809,804 | B1 | 10/2004 | Yount et al. ................... 356/73 |
| 6,815,172 | B1 | 11/2004 | Martinez et al. ........... 435/7.32 |
| 2002/0122612 | A1 | 9/2002 | Walt et al. ..................... 385/12 |
| 2002/0164271 | A1 | 11/2002 | Ho .......................... 422/82.08 |
| 2003/0008410 | A1 | 1/2003 | Hechinger .................. 436/172 |
| 2003/0207461 | A1 | 11/2003 | Bell et al. .................... 436/172 |
| 2004/0077100 | A1 | 4/2004 | Sekar et al. ................. 436/172 |

OTHER PUBLICATIONS

Reynolds, G.A., *Stable Heptamethine Pyrylium Dyes That Absorb in the Infrared*, J. Org. Chem., vol. 42, No. 5, 885–888 (1977).

Sosnovskii, G.M., *Synthesis of Meso–Substituted Tricarbocyanine Dyes With An Ortho–Phenylene Bridge In The Chromophore*, Journal of Organic Chemistry of the USSR, vol. 19, No. 10, 1861–1864 (1983).

Makin, S.M., *Aminoformylation of Unsaturated Aldehydes 2–Alkoxyaldehyes and Their Acetals, and Keytones of the Alicyclic Series*, Journal of Organic Chemistry of the USSR, vol. 13, No. 6, 1093–1096 (1977).

Webb, J.P., *Sixteen New Infrared Laser Dyes Excited By A Simple Linear Flashlamp*, Eastman Organic Chemical Bulletin, vol. 46, No. 3, 1–6 (1974).

Russian reference by Tolmachev et al. (full cite is in Russian).

Narayanan, N., *A New Method for the Synthesis for Heptamethine Cyanine Dyes: Synthesis of New Near–Infrared Fluorescent Labels*, J. Org. Chem. 60, 2391–2395 (1995).

Strekowski, L., *Functionalization of Near–Infrared Cyanine Dyes.*, Heterocyclic Chem., 33, 1685–1688 (1996).

Narayanan, N., *New Near Infrared Dyes for Applications in Bioanalytical Methods*, SPIC vol. 2388, 6–15 (1995).

Pierce, Brian M., *Lasing Properties of Several Near–IR Dyes for a Nitrogen laser–Pumped Dye Laser with an Optical Amplifier*, IEEE Journal of Quantum Electronics, vol. QE–18, No. 7 (1982).

* cited by examiner

PARTICLES FOR USE IN A DETECTION SYSTEM

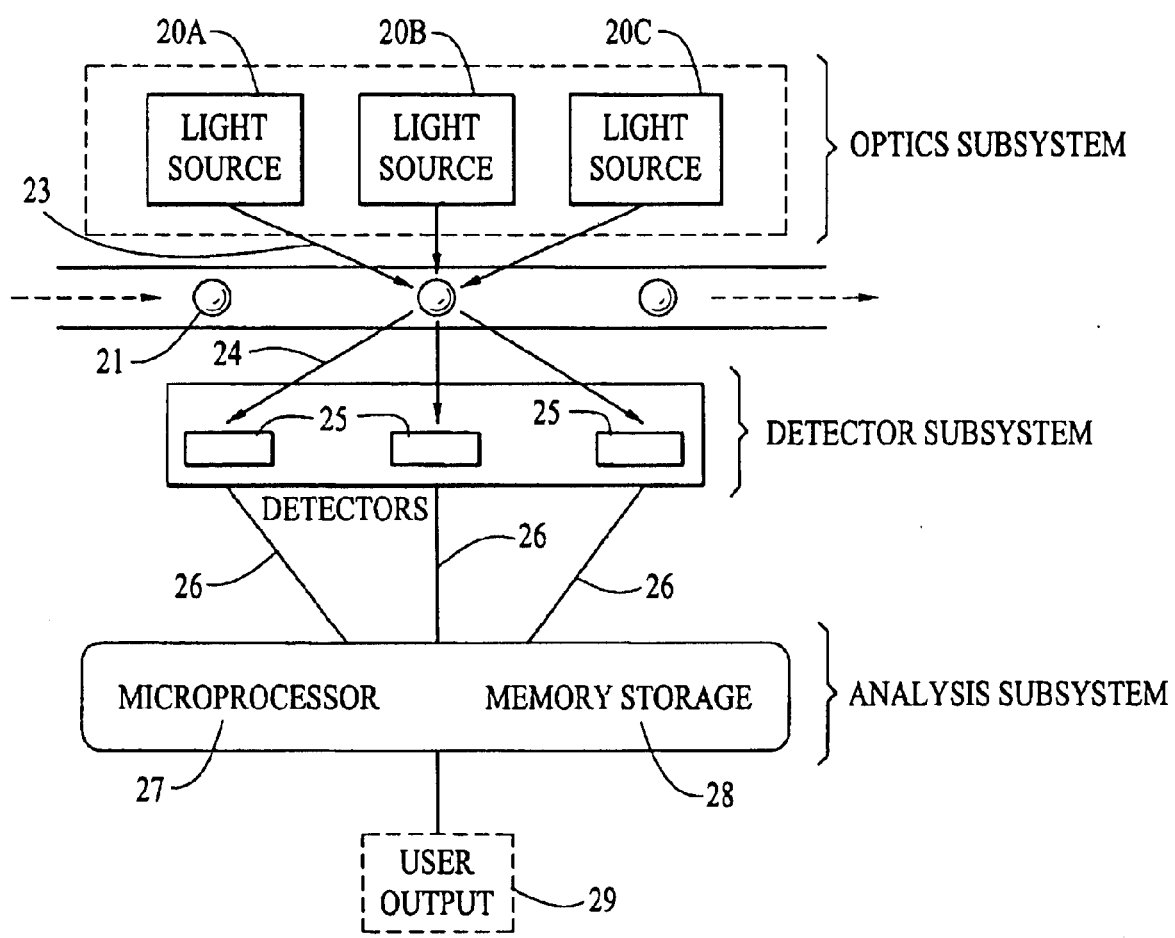

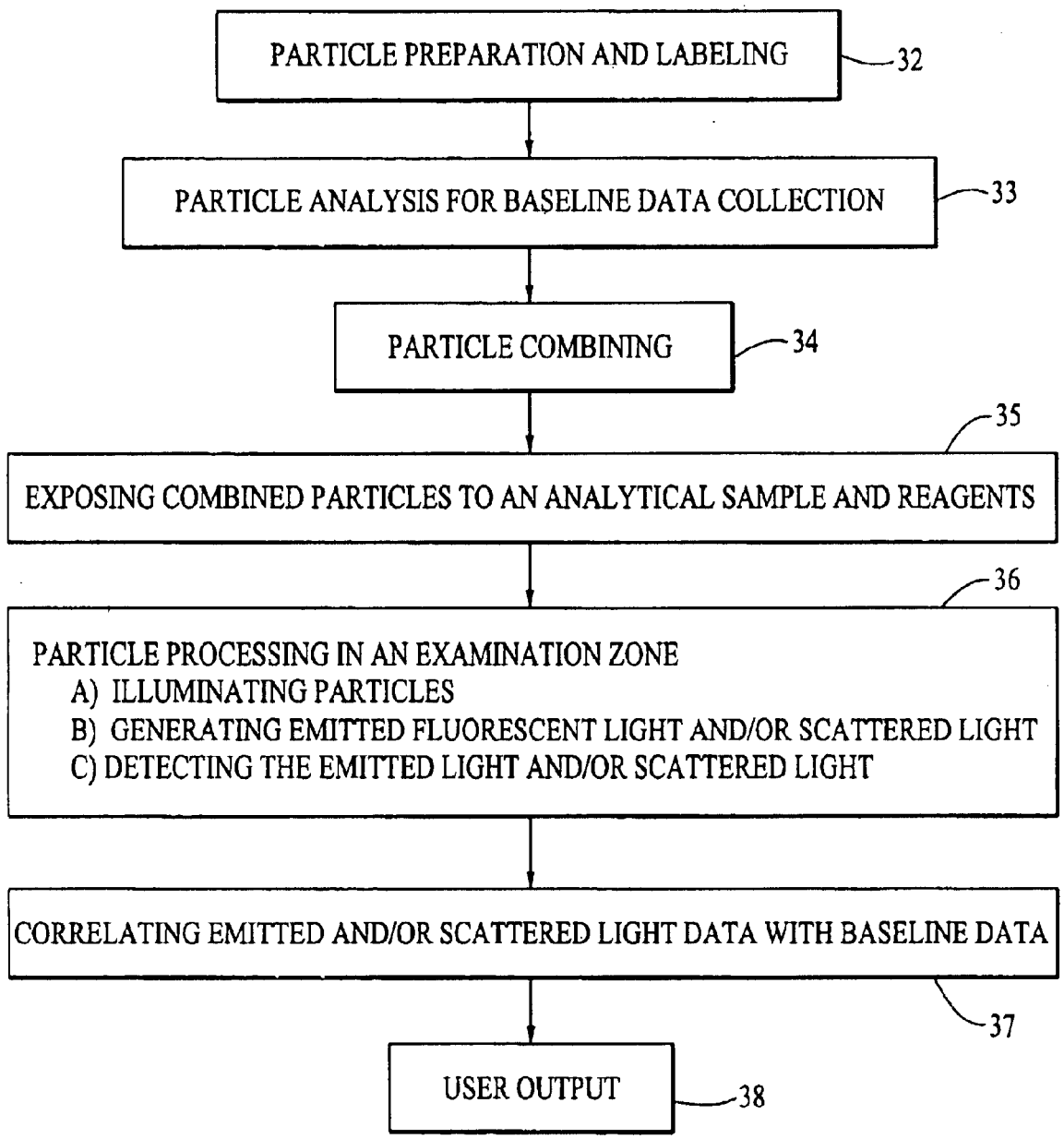

EMISSION SPECTRA OF IR792 PERCHLORATE IN METHYLENE CHLORIDE CHLORIDEFOR TWO MONTH PERIOD (STABILITY STUDY)

EMISSION SPECTRA OF COMPOUND 6 IN METHYLENE CHLORIDE FOR TWO-MONTH PERIOD (STABILITY STUDY)

(CPS) / WAVELENGTH (NM)
FILE # 4 = ISA52805
INFRARED EMISSION ACQUISTION, USED T DETECTOR;
IR:YL=0:4, ~1e-6M, IN MC, EX:782NM

OVERLAY Y-ZOOM CURSOR
2/28/00 11:25 AM RES=NONE

EMISSION SPECTRA OF IR792 PERCHLORATE AND COMPOUND 6 IN METHYLENE CHLORIDE

EMISSION SPECTRA OF IR792 PERCHLORATE AND COMPOUND 6 MIXTURE IN METHYLENE CHLORIDE.

(CPS) / WAVELENGTH (NM)
FILE # 1 = ISA52406
INFRARED EMISSION ACQUISTION, USED T DETECTOR;
IR:YL=4:0, ~0.163e-6M IN MC; LASER

OVERLAY Y-ZOOM CURSOR
2/22/00 2:44 PM RES=NONE

EMISSION SPECTRA OF ETH 5294 AND IR792 PERCHLORATE MIXTURE IN METHYLENE CHLORIDE. EXCITATION WAVELENGTH IS AT 539 NM

EMISSION SPECTRA OF ETH 5294 AND COMPOUND 6 MIXTURE IN METHYLENE CHLORIDE. EXCITATION WAVELENGTH IS AT 539 NM

UNCORRECTED FLUORESCENCE SIGNALS OF POLYSTYRENE PARTICLES CONTAINING DIFFERENT CONCENTRATIONS OF COMPOUND 5a

CORRECTED FLUORESCENCE SIGNALS OF POLYSTYRENE PARTICLES CONTAINING DIFFERENT CONCENTRATIONS OF COMPOUND 5b. MEASUREMENTS WERE MADE OVER 35 DAYS IN THE PROTOTYPE CyXL FLOW CYTOMETER

CORRECTED FLUORESCENCE SIGNALS OF POLYSTYRENE PARTICLES CONTAINING DIFFERENT CONCENTRATIONS OF COMPOUND 5d

ANALYTE DETECTION SYSTEM

This application is a division of Ser. No. 09/990,678 filed Nov. 11, 2001, now U.S. Pat. No. 6,838,289.

BACKGROUND

The present invention relates to a detection system and method for measuring fluorescently labeled analytes by their interactions with particles encoded with fluorescent labels, and further relates to fluorescent label compositions for coding polymeric microbeads or particles.

Polymeric beads are useful analytical tools for detecting and measuring various analytes especially when combined with flow cytometry systems and methods. The term polymeric beads is referred to in the art and used hereinafter interchangeably as beads, particles, microbeads, microparticles, and microspheres. Analytes of interest are often bound to a particle and identified by a corresponding characteristic of the particle such as size, magnetism, and spectroscopic properties including absorbance, light scatter, color, and fluorescence at one or more wavelengths.

For example, prior art patents describe the use of particle size or color as parameters for distinguishing between subpopulations of particles. A disadvantage of employing size or color as a distinguishing markers is that these systems permit the labeling of only a few distinct subpopulations of particles. Employing additives of differing absorbance to mark different particle subpopulations has also been described. A disadvantage of absorbance markers is that absorbance in a particle is difficult to measure and is not a particularly sensitive method of detection.

Fluorescence characteristics of particles or cells has been described in a variety of analytical systems including fluorescence microscopes, flow cytometers and image microscopes for analyte identification. Fluorescent labels are desirable markers for coding particles and have been described in a variety of different approaches including employing single and multiple fluorescers as labels. The use of fluorescent labels as markers in flow cytometry systems is described, for example, in U.S. Pat. Nos. 4,745,285; 5,028,545; 5,682,038; and 5,880,474, all of which are incorporated herein by reference. However, there are several distinct disadvantages to prior systems.

As with particle size, the use of a single fluorescent marker by itself enables labeling of only a few distinct subpopulations of particles. Prior systems employing multiple fluorescent labels can be disadvantaged when separate space is not reserved for the emission spectra for the analyte of interest. Overlapping emission spectra between an analyte and a fluorochrome can hinder detection and quantification of the analyte in these systems.

Many naturally occurring samples and materials for instrument construction contain materials, which fluoresce in the UV or the short-wavelength end of the visible spectrum. These extraneous sources of fluorescence interfere with particle detection and with accurate detection and quantification of analytes by fluorescent labeling.

When multiple fluorescent labels are used, the multiple fluorescent emission spectra may be indistinct due to dye to dye interactions, overlapping spectra, and non-Gaussian emission profiles. Indistinct emission spectra make accurate identification and quantification between multiple subpopulations of particles difficult. Interaction between multiple fluorescent labels limits the number of distinguishable particle species and interaction between the fluorescent labels and fluorescent analytical dyes limits the quantitative detection capabilities of the device. Complex signal processing devices must be employed to compensate for the indistinct spectra, adding to the cost of the detection system.

Prior analytical detection systems employing particle technology suffer from one or more of the following disadvantages: 1) limited accuracy; 2) limited sensitivity; 3) inadequate numbers of labels for the multitude of analytes to be detected; 4) expensive equipment; and 5) time consuming multiple reaction steps. A need, therefore, exists for an analytical detection system employing particle technology that can distinguish between multiple subpopulations of particles in a cost and time efficient manner while simultaneously accurately identifying and quantifying multiple analytes.

SUMMARY

The present invention is for an analyte detection system that satisfies this need. The system employs particles having a fluorescent analyte detection dye and a combination of fluorescent particle labels. The fluorescent particle labels are excited by light at the same excitation wavelength and the fluorescent analyte detection dye is excited by light at a different excitation wavelength. One of the excitation wavelengths is in the near infrared region (NIR). The emission spectra of the fluorescent labels have a maximum wavelength and the maximum wavelengths are distinguishable such that a combination of relative amounts of fluorescent labels used for a particular set of particles can be used to differentiate that set of particles from another set of particles with a different combination of relative amounts of fluorescent particle labels. Each particle can also have a second analyte detection dye, excited by light at the same or a different wavelength as the first analyte detection dye on the particle.

When multiple populations of particles are used, individual sets of particles can have different fluorescent analyte detection dyes. The different fluorescent analyte detection dyes also have distinguishable emission spectra and can be excited by the same or a different exciting light. The particles can be differently sized and the size of the particles can be used as a factor to differentiate between multiple populations of particles.

The particles in this analyte detection system can have an analyte specific receptor that forms a complex with the analyte. The receptor-analyte complex can contain the fluorescent analyte detection dye, detectable by the system. The analyte detection system can alternately have a second receptor, which forms a dual receptor-analyte complex on the particle. This complex also contains the fluorescent analyte detection dye, detectable by the system.

In a method according to the present invention, a population of particles, as described above, is moved through an examination zone, such as in a flow cytometer. An exciting light of a first wavelength is directed at each particle in the examination zone. An exciting light of a second wavelength is also directed at each particle in the examination zone. The emitted lights of the fluorescent analyte detection dye(s) and fluorescent labels are detected and the detected emitted light is correlated to the particle under analysis.

When multiple subpopulations of particles are employed in the invention, the fluorescent analyte detection dyes can be excited either by the same excitation laser system, or by different excitation lasers. When different excitation lasers are utilized in this system, an exciting light of a third excitation wavelength is also directed at each particle in the examination zone and the emitting light corresponding to this fluorescent analyte detection dye is also detected and correlated with the particle under analysis.

When the populations of particles are differently sized and the size of the particles is used as another factor to differentiate between multiple populations of particles, one of the exciting lights generates a scattered light, which is detected and correlated with the particle under analysis as well as the detected emitted light.

The fluorescent labels employed in the invention can be cyanine dyes that have maximum emitting wavelengths in the NIR of the spectrum. The cyanine dyes used in the analyte detection system can be ring-locked benzoindotricarbocyanine compounds, which are incorporated into the particles in combinations of two or more than two, to label the particles, and distinguish each particle or population of particles having the same combination of fluorescent labels from other particles with a different combination of fluorescent labels.

DRAWINGS

FIG. 2 is a schematic illustration of an exemplary flow cytometry system in accord with the present invention.

FIG. 3 is a flow chart of a method practiced using the particle detection system as exemplified in FIG. 1 and incorporating the present invention.

DESCRIPTION

Figure 1A:
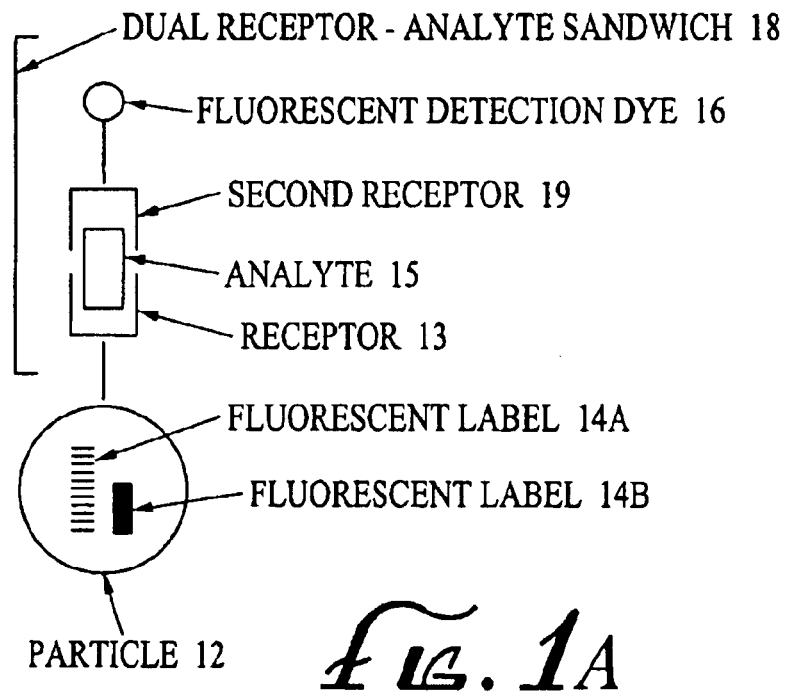
FIG. 1 is an illustration of an exemplary particle for use in a multi-analyte particle based detection system according to the present invention where particle 1 illustrates a particle-receptor-analyte-receptor complex, and particle 2 illustrates a particle-receptor-analyte complex.

The present invention provides particles for use in a a fluorescence based assay system and the fluorescent labels employed in the assay system. The assay system can distinguish between numerous sub-populations of particles and quantify multiple analytes of interest. The fluorescent labels employed in the assay system are excited by a common source and emit at distinguishable wavelengths from themselves and other fluorescent sources in the system, and have excitation wavelengths in the far-red or near-infrared region of the spectrum.

According to the present invention, multiple analytes are simultaneously detected and measured by combining microfluidics and fluorescent particle sensor technology. Multiple analytical reactions are isolated onto a set of micrometer scale particles, which are read individually by a device such as a flow cytometer. The device determines the identity of each set of particles and the extent to which each particle has reacted with its analyte. Each set of particles: 1) carries a unique combination of fluorescent labels to code the particles; 2) is specific to an analyte, or class of analytes of interest; and 3) contains a fluorescent dye for identifying individual analytes of interest (i.e., an analytical dye, or a fluorescent analyte detection dye).

According to the method of the present invention, an analytical sample is allowed to react with a set of particles specific to various analytes of interest. The particles are then passed through a detection device. Particles that have reacted with their specific analyte of interest generate fluorescent emission spectra corresponding to the fluorescent dye associated with the particular particle and analyte of interest. The device identifies the particles at least partly by a unique combination of fluorescent labels incorporated into the particles. The information from the fluorescent labels is correlated with the information from the analyte specific fluorescent dye and the corresponding results allow quantitative identification of multiple analytes in one reaction.

An aspect of the detection system and methods described herein is the preparation and use of appropriately labeled particles. The particles employed in the present invention are generally made of polymeric materials such as a polystyrene. Suitable preparation techniques are generally known to those skilled in the art to make beads/particles that are useful in the present invention. An example of a suitable preparation technique is described in U.S. Pat. No. 4,609,689, incorporated herein by reference. Alternatively, the beads/particles may be obtained from a commercial supplier such as Bio-Rad Laboratories Inc., or Bangs Laboratories Inc.

The fluorescent labels employed in the invention are preferably, but not required, embedded within the particle. Internally embedding the fluorescent labels in the particle increases signal stability by shielding the labels from environmental factors that cause fluorescence degradation. Internally embedding the fluorescent labels in the particle also reserves the exterior of the particle for binding analytes and/or analytical dyes.

The fluorescent labels are added to the particles by using methods known to those in the art. One known method is a casting process, such as the casting process described in U.S. Pat. Nos. 4,302,166 and 4,162,282, which are incorporated herein by reference. In this process, a fluorescent label and a polymer are dissolved in a solvent. The solution is expelled as a stream through a fine nozzle into a sheath of water. A piezoelectric transducer breaks the stream up into discrete droplets that cure into particles as the solvent diffuses into the water. Another process is the swell-shrink method. This method, which is incorporated herein by reference, is described by L. B. Bangs (Uniform Latex Particles; Seragen Diagnostics Inc. 1984, p. 40). The swell-shrink process consists of adding an oil-soluble or hydrophobic dye to stirred particles and after an incubation period, any dye that has not been absorbed by the particles is washed away.

A set of particles is distinguishable from another set of particles on the basis of a unique combination of fluorescent labels for coding the particles. Multiple sets of particles can be used to specifically detect multiple analytes in a single reaction. Detecting multiple analytes in one reaction can simplify multiple assay procedures and result in less variability between results arising from separate assays.

In the present invention, differing amounts of fluorescent labels are used in varying combinations in different sets of particles to identify an individual set of particles from another set of particles. It is preferable, but not required, that the particles are labeled with at least two fluorescent labels and greater numbers of label combinations can be used to create greater numbers of particle populations. For example, a particle containing one part label A and two parts label B is distinguishable from a second particle containing two parts label A and one part label B. These particles are distinguishable from a third particle containing two parts label A and four parts label B or four parts label A and two parts label B. Pairs of fluorescent labels can be used in this manner to multiply the number of distinguishable particle populations. Accordingly, if an analytical detection system is capable of distinguishing ten different amounts of label A, then label A alone could be used to differentiate only ten different particle populations. However, if an analytical detection system can additionally distinguish between ten different amounts of label B, label A and label B can be used in combination to fluorescently label the identities of ten times ten, or one hundred different particle populations. If a third label is employed, the number of identifiable particles expands to one thousand distinguishable particle populations.

For an optimal number of distinct particle species it is advantageous that the emission spectra of the fluorescent particle labels accurately correspond to the concentrations of different fluorescent labels employed in particular particle sets. For accurate identification and quantification of multiple analytes on particles by fluorescence it is also advantageous that there is minimal interference between extraneous sources of fluorescence, the fluorescent labels employed in the assay, and the fluorescent dye associated with the analyte. Prior detection systems and methods have failed to provide a fluorescence based detection system that simultaneously provides these advantages.

Particle size is another parameter for coding particles. Particles may be commercially purchased in preformed sizes or prepared in different homogenous sizes. Preferred, but not required sizes of beads are 5.5, 7.0, and 10.2 microns. The size of a particle can separately be detected and determined apart from fluorescence and correlated, along with the fluorescent labels, with the analyte detection dye to detect and quantify an analyte of interest. If fewer numbers of coded particles are needed, a combination of fluorescent labels to mark particles is preferred. As shown below in Table 1, size and multiple fluorescent labels expand the number of distinguishable particles. In Table 1, three different combinations of relative fluorescent concentrations are used. When two different particles sizes are also used, this expands the number of distinguishable populations of particles to six.

TABLE 1

Particle Size as an Additional Particle Coding Parameter.

| Particle Number | Size | Particle A (Relative Amount) | Particle B (Relative Amount) |
|---|---|---|---|
| 1 | 1 | 1 | 1 |
| 2 | 1 | 1 | 3 |
| 3 | 1 | 3 | 1 |
| 4 | 2 | 1 | 1 |
| 5 | 2 | 1 | 3 |
| 6 | 2 | 3 | 1 |

The concentration of the fluorescent labels in the particles is proportional to the magnitude of the emission signal. The maximum number of distinguishable particle combinations is achieved by preparing particles with the same magnitude of emission signals. It is desirable, but not required, that the magnitude of the emission signals of different sets of particles of different sizes are of the same approximate magnitude. To achieve this objective, the concentration of fluorescent labels in small particles is increased, and/or the concentration of fluorescent labels in large beads is decreased. The emission wavelengths of the fluorescent labels used in the invention are in the near-infrared region of the electromagnetic spectrum. For purposes of this disclosure, the near infrared region of the electromagnetic spectrum is light having a wavelength greater than 750 nm and less than 1000 nm. Marking particles with fluorescent labels with longer emission wavelengths in a series of fixed predetermined amounts and the means to accomplish is an improvement in the art. The absorbance and emission spectra of these fluorescent labels are well removed from the spectra of common interferents. The long emission wavelengths of the fluorescent labels employed in the present invention enable a large selection of sensing dyes to be employed as the analytical signal for detecting multiple analytes of interest. Accordingly, fluorescent dyes having emission wavelengths less than 750 nm can be included as candidates for analytical sensing dyes without consideration of overlapping emission spectra with the fluorescent labels.

It is desirable, but not required, that the fluorescent labels are stable, both in the solvents employed for preparing the coded particles and in the particles themselves during storage and use. This includes conditions of use wherein the particles are repeatedly heated almost to the boiling point of water. Also, it is desirable, but not required, that the fluorescent labels to be employed for coding particles are soluble in the solvents required for infusing them into the particles. The fluorescent labels advantageously do not leach out of the particles during extended storage in aqueous media, or during high temperature processes employed in various assays such as DNA amplification.

It is also desirable, but not required, that the fluorescent labels in a set do not significantly interact through energy transfer, even when embedded in a single particle. Such interactions can result in inaccurate fluorescence detection (e.g., an apparent loss of fluorescence of a shorter wavelength dye in the presence of a longer wavelength dye). These types of interactions may complicate simultaneous use of the dyes as particle labels. Further, the fluorescent labels advantageously do not have significant interference with fluorescent dyes used as the analytical dye such as ETH 5294, a fluorescent pH indicator in particle optodes for measurement of target cations.

It is advantageous, but not required, that the fluorescent labels share the same excitation laser. The detection system is generally more compact when the same excitation laser is employed in the system and the use of one laser to excite the fluorescent label combination is generally more economically efficient. However, multiple excitation lasers may be employed in the detection system to excite the fluorescent label combinations in alternate embodiments.

The emission wavelengths of the fluorescent labels, when used in combination in a particle, are generally distinguishable from one another, but can have overlapping portions. A distinguishable fluorescent label combination is such that one particular particle with one combination of fluorescent labels can be identified or differentiated from another particle with a different combination of fluorescent labels by the particular emission spectra of each particle. For example, a first particle can be identified by comparing the relative magnitude of the spectral emissions of the fluorescent labels in that particle. This particle can be distinguished from a second particle that has a different relative magnitude of spectral emissions for the fluorescent labels in that particle. Fluorescent label combinations employing fluorescent labels with spectral emission maxima that differ from one another by about at least a 30 nm Stokes shift are generally distinguishable. However, this is not a requirement of the present invention and the precise separation of the fluorescent label spectral emission maxima required to practice the invention can differ with each particular combination of labels and the spectral resolution.

Employing the above described fluorescent labels in the assay system solves the limitations of prior fluorescence based detection systems in that: 1) the emission signals of the particles do not significantly interact with each other; 2) the analyte emission signals do not significantly interact with the emission signals of the particle; and 3) the emission signals of the particles and the analytes do not significantly interact with extraneous sources of fluorescence. In addition to the advantages recited above, the use of long wavelength fluorescers as labels permits the use of inexpensive and compact diode lasers and economical photon detectors.

Near infrared fluorescent compounds are known to those skilled in the art and can be employed in the present invention as fluorescent labels for coding particles. Suitable fluorescent compounds are selected according to the above criteria by methods known to those skilled in the art and can be employed in the present invention. For example, Webb, J. P., et al., *Eastman Organic Chemical Bulletin*, (1974), Vol. 46, No. 3; Pierce, B. M., et al., *IEEE Journal of Quantum Electronics*, (July 1982), Vol. QE-18, No. 7, pp. 1164–1170; Strekowski, et al., *J. Org. Chem.*, (1992), Vol. 57, pp. 4578–4580; and U.S. Pat. Nos. 2,887,479; 2,895,955; and 5,061,618, the disclosures of which are incorporated herein by reference, describe near infrared fluorescent compounds.

Cyanine dyes are preferably, but not required, used as fluorescent labels for coding particles due to their stability, solubility, and absorbance and emission in the near infrared region (NIR). The basic structure of the cyanine chromophore is represented by Structure A, as shown below:

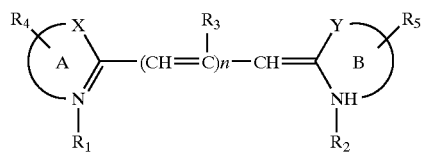

Structure A. The Cyanine Chromophore.

The cyanine chromophore represented above contains a flexible polymethine chain, where n represents an integer. The half circles in the above structure represent enough carbon atoms to make up cyanine nuclei. Examples of cyanine nuclei include substituted or unsubstituted thiazole, benzothiazole, napthothiazole, benzoxazole, napthoxazole, benzolselanazole, napthoselenazole, indole, and benzoindole rings. Other nuclei are known to those skilled in the art and can also be employed in the fluorescent labels used in the invention.

Preferably, but not required, modified cyanine compounds are employed as labels for coding particles. The chemical modification consists of ring-locking the flexible cyanine chromophore with a cycloalkenyl ring. Structure B as shown below represents preferable ring-locked tricarbocyanine chromophores used in the detection system.

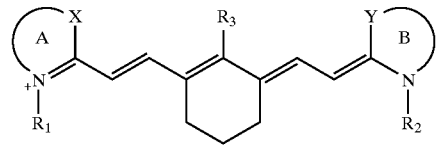

Structure B. A Ring-Locked Tricarbocyanine Chromophore.

Benzo-indotricarbocyanine dyes containing a ring-locking cyclohexenyl group in the cyanine chromophore have been prepared. These cyanine compounds are represented by Structure C as shown below.

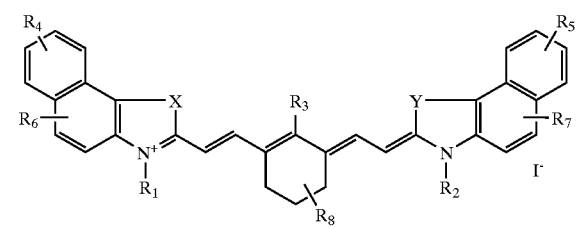

Structure C. Ring-Locked Benzo-indotricarbocyanine Compounds.

In the above Structures A–C:

Rings A and B represent ring structures with sufficient carbon atoms to make up a cyanine nuclei;

n is an integer;

X and Y are each independently selected from the group consisting of O, S, $NR_9$, and $CR_9R_{10}$;

$R_1$ and $R_2$ are each independently selected from the group consisting of H, $C_1$–$C_{20}$ alkyl, $C_1$–$C_{20}$ haloalkyl, $C_1$–$C_{20}$ alkylene, or $C_1$–$C_{20}$ haloalkylene;

$R_3$ is selected from the group consisting of H, halogen, OH, $OR_{11}$, $SR_{11}$, $NR_{11}R_{12}$, $C_1$–$C_6$ alkyl, $C_1$–$C_6$ alkylene, $C_3$–$C_6$ cycloalkyl, $C_3$–$C_6$ cycloheteroalkyl, $C_3$–$C_6$ cycloalkylene, $C_3$–$C_6$ cycloheteroalkylene, phenyl, biaryl, heteroaryl, or heterobiaryl, wherein the $C_1$–$C_6$ alkyl, $C_1$–$C_6$ alkylene, $C_3$–$C_6$ cycloalkyl, $C_3$–$C_6$ cycloheteroalkyl, $C_3$–$C_6$ cycloalkylene, $C_3$–$C_6$ cycloheteroalkylene, phenyl, biaryl, heteroaryl and heterobiaryl groups may be substituted with halogen, OH, $C_1$–$C_4$ alkyl, or $C_1$–$C_4$ haloalkyl;

$R_4$, $R_5$, $R_6$, and $R_7$ are each independently selected from the group consisting of halogen, OH, $C_1$–$C_4$ alkyl, or $C_1$–$C_4$ haloalkyl, phenyl, or heteroaryl, or other aromatic substituents known to those skilled in the art;

$R_8$ is selected from the group consisting of $C_1$–$C_4$ alkyl, or $C_1$–$C_4$ haloalkyl;

$R_9$ and $R_{10}$ are each independently selected from the group consisting of hydrogen, $C_1$–$C_4$ alkyl, or $C_1$–$C_4$ haloalkyl;

$R_{11}$ and $R_{12}$ are each independently selected from the group consisting of $C_1$–$C_6$ alkyl, $C_3$–$C_6$ cycloalkyl, phenyl, biaryl, heteroaryl, or heterobiaryl, wherein the $C_1$–$C_6$ alky$_1$, $C_1$–$C_6$ cycloalkyl, phenyl, biaryl, heteroaryl, and heterobiaryl groups may be substituted with halogen, OH, $C_1$–$C_4$ alkyl, or $C_1$–$C_4$ haloalkyl, or when $R_3$ represents $NR_{11}R_{12}$, $R_{11}$ and $R_{12}$ may be taken together to form an optionally substituted $C_3$–$C_6$ aliphatic or $C_3$–$C_6$ aromatic heterocyclic ring.

The above representations serve to exemplify various modifications of the benzo-indotricarbocyanine compounds that can be used in the detection system. However, other substitutions in various positions on the structure are available and it is understood that the scope of suitable compounds is not limited by the above representations.

The synthesis of cycloalkenyl cyanine dyes known in the art. These cyanine compounds are prepared by the reacting a heterocyclic base containing an activated alkyl group and either an amino-pentadienylidene-ammonium salt or an unsaturated bisaldehyde. See, e.g., Slominski, Yu. L., et al., *Zh. Org. Khim.*, (1983), Vol. 19, 2134; Narayanan, N., *J. Org. Chem.*, (1995), Vol. 60, pp. 2391–2395, the disclosures of which are incorporated by reference. These preparations are represented below in Scheme 1 in the preparation of benzo-indotricarbocyanine compounds useful in the present invention as a fluorescent labels for coding particles.

Scheme 1
Synthesis of Ring-locked Benzo-indotricarbocyanine Compounds.

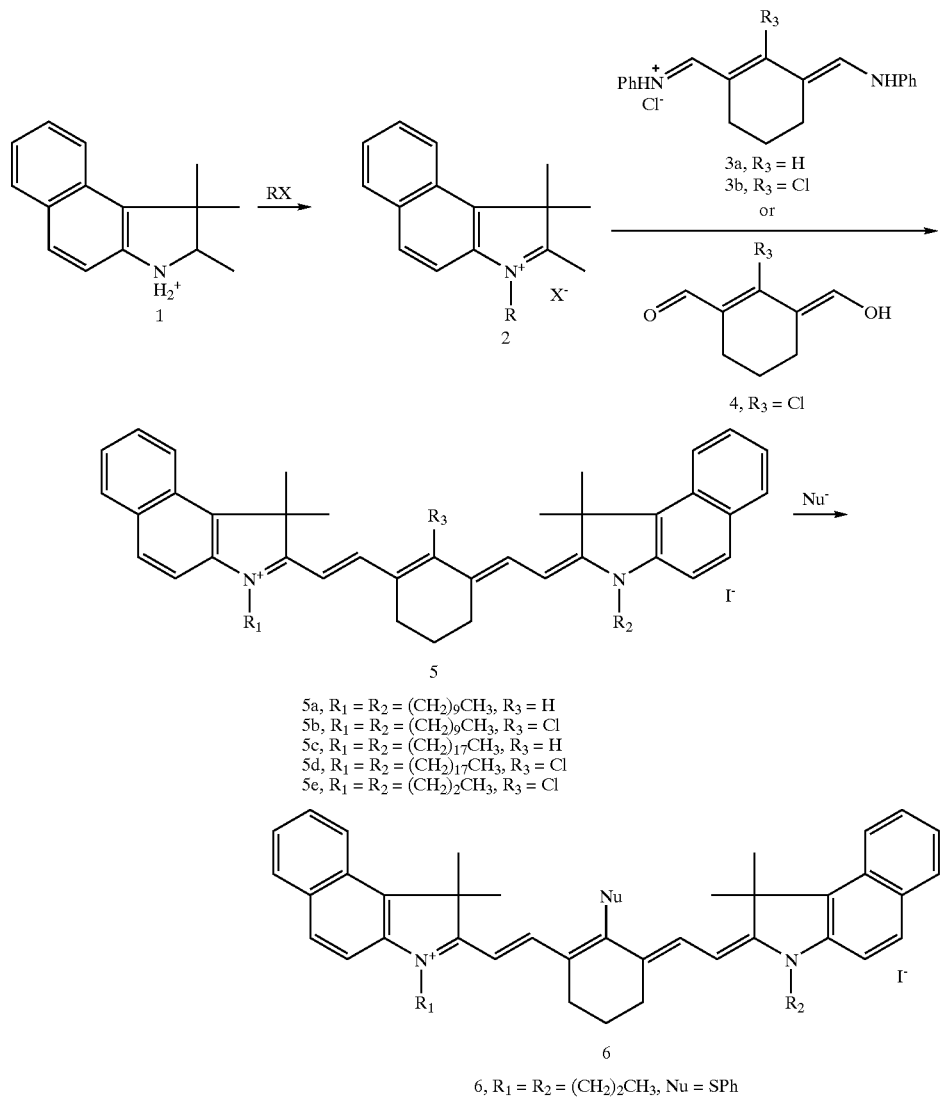

The benzo-indotricarbocyanine compounds such as those shown in Scheme 1 and represented in Structure C are prepared by the reaction of a 1, 1,1,2-trimethyl-1H-benzo (e)indole with an alkyl halide to produce a compound such as 2, a 2,3,3-trimethy-1-alkyl-3-H-benzindolenium halide. Compound 2 is then allowed to react with either a pentamethine salt (3a, 3b), or a bisaldehyde (4) to produce a corresponding benzo-indotricarbocyanine compound (e.g., 5a–e). Where a halogen substitutent is present on the cyclohexenyl ring in the cyanine chromophore, the compounds may be derivatized by addition of a nucleophile as shown in the reaction of 5e to 6. Derivatization to compounds such as 6 is known in the art and other substitutions may be made according to known methods. See, e.g., Strekowski, et. al., J. Org. Chem., (1992), 57, 4578–4580.

Figure 1B:
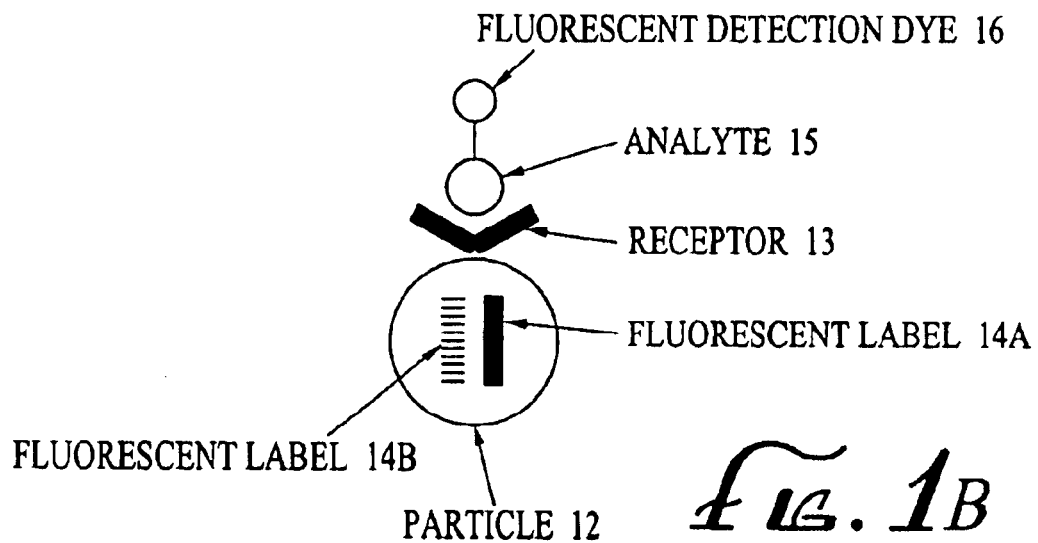

Exemplary particles for use in a multi-analyte detection system are shown in FIG. 1. As illustrated in FIG. 1, particles 12 are labeled with a fluorescent labels 14A, 14B and an analyte receptor 13 is attached to the particle. The particle, 14A or 14B containing the analyte receptor 13 is then used to assay a particular sample for an analyte 15 of interest. A fluorescent analyte detection dye 16 is also present. The analyte detection dye 16 emits a fluorescent signal when the analyte specific to the receptor is also present in the sample.

Fluorescent analyte detection dyes are known to those of skill in the art. The fluorescent analyte detection dye can be a single fluorescer or a donor-receptor dye pair that is activated by energy transfer in the detection system and can be synthetic or a naturally occurring fluorescer. Appropriate fluorescent analyte detection dyes can be selected for a particular assay and used in accordance with the present invention by those of skill in the art with reference to this disclosure.

The fluorescent analyte detection dyes are complexed to the particle by various methods known to those skilled in the art depending on the particular assay employed in a specific analytical reaction. For example, the fluorescent analyte detection dye 16 can be attached to a receptor (not shown), or to an analyte 15 (FIG. 1B), or the analyte can contain a naturally occurring fluorochrome (not shown). The fluorescent analyte detection dye can also be attached to a second receptor in a dual receptor-analyte complex, (e.g., a "sandwich"), as exemplified in FIG. 1A.

The detection system described herein can be used to detect and quantify analytes in assays known to those skilled in the art employing polymeric bead technology. In general, the invention is suitable for assays that include coupling, either passive or covalent of an analyte to an analyte-specific polymeric surface such as a polymeric bead or particle and detection of the analyte by fluorescence. A variety of protocols are known to those skilled in the art for detecting various analytes either by a direct or indirect signal producing system involving a labeled conjugate. The analyte need not be present on the particle in the detection system. The analyte can couple to a portion of the analyte-specific receptor and consume a portion of the analyte-specific receptor, leaving the fluorescent portion of the complex, which is then detected by the particle detection system.

For purposes of this disclosure, the term analyte includes, but is not limited to organic or inorganic molecules capable of interaction with an analyte-specific receptor on a particle and detection by fluorescence. The term analyte, as used herein, also refers to analyte-reactant pairs, analytical reactants, and other molecules that interact with the analyte to produce the fluorescent detection. Examples of analytes include antibodies, antigens, cells, DNA and DNA fragments, electrolytes, enzymes, haptens, metabolites, microorganisms, and other biomolecules as well as non-biomolecules capable of interaction with an analyte-specific receptor on a particle and detection by fluorescence.

The present invention can be employed in detecting and measuring analytes for uses such as serology, determination of infectious disease exposure, diagnostic assays such as determining naturally occurring levels of mammalian hormones and electrolytes, and other assays such as therapeutic drug administration, monitoring, and research, as well as oligonucleotide assays.

Examples of antigens that can be detected by the present invention include but are not limited to naturally and unnaturally occurring hormones, and therapeutic drugs. Examples of electrolytes that can be detected by the present invention include but are not limited to sodium, potassium, calcium, and chlorine. Examples of enzymes that can be detected by the present invention include but are not limited to amylase and alkaline phosphatase. Examples of metabolites that can be detected by the present invention include but are not limited to glucose, cholesterol, and creatinine. Cells, cell fragments, and micororganisms that can be detected according to the present invention include but are not limited to viruses, bacteria, fungi, animal and mammalian cells and fragments thereof. Examples of oligonucleotides that can be assayed by the present invention include mutated and non-mutated genetic sequences, such as genetic markers and genetic sequences of infectious diseases.

The term receptor as referred to herein includes analyte-specific reactants capable of binding or complexing to a polymeric particle. This includes but is not limited to fluorescent reporter molecules capable of reacting with an analyte, and specific-binding pair members for detection of analytes such as specific microorganisms and cells. Another example of a receptor includes monoclonal antibodies attached to the surface of the particle to serve as antibody catchers. An epitope recognized by the antibody, is bound, followed by labeled antibodies specific to the epitope. Other receptors are known to those of skill in the art. The particular use of various receptors in the analyte detection system of the present invention will be understood by those of skill in the art with reference to this disclosure.

An advantage of the invention is that multiple analytes may be detected simultaneously in an automated system. For example, a panel of particles may be prepared, composed of multiple subpopulations of particles, where each individual subpopulation of particles is specific to a different analyte of interest. The panel of particles is allowed to react with a test sample and then passed through the detection system. In this manner, a panel of analytes may be simultaneously detected and quantified. Thus, the invention is time efficient in that multiple assays may be completed in one reaction. Examples of panels known to those skilled in the art that may be used with the invention include electrolyte panels, hormone panels, and such. It is understood that other multi-analyte panels are known to those with skill in the art, and can be employed in the detection system of the present invention, with reference to this disclosure.

A preferred assay system employed in the present detection system and methods is a flow cytometer. Flow cytometry systems are known to those in the art. A preferred flow cytometer is a modified Coulter XL flow cytometer with a 785 nm laser replacing the standard argon ion laser. The flow cytometer operates in the conventional manner known as will be understood by those with skill in the art with reference to this disclosure.

FIG. 2 is an exemplary schematic illustration of a flow cytometry system that can be used in the present invention.

Light energy 23 is provided in the flow cytometer by exciting light sources 20A, 20B and 20C, such as a laser or an arc lamp, in the optics subsystem. Preferably, a longer wavelength excitation laser is used to simultaneously excite the fluorescent labels, used to mark the particles 21, and one or more shorter wavelength excitation lasers are used to excite the fluorescent analyte detection dyes. The optics subsystem of the cytometry device can include appropriate laser line filters, beam expanders, mirrors, lenses, and flowcells, as well as other components advantageous in operating a cytometry device as will be understood by those with skill in the art with reference to this disclosure.

Appropriate lower wavelength lasers for excitation of the analyte dyes are known to those skilled in the art. A preferred excitation wavelength for the fluorescent analyte detection dyes is a 635 nm diode laser, alternatively, a 650 nm diode laser, or a 633 nm helium-neon laser can be used. Alternatively, a lower wavelength 488 nm argon-ion, or a 530 nm doubled YAG laser can be used. In another aspect of the invention, multiple detection lasers can be used to detect. multiple fluorescent dyes at different excitation wavelengths. In this aspect of the invention, a combination of a higher wavelength laser with a lower wavelength laser is used. An example of this aspect of the invention is a 650 nm laser and a 530 nm laser, used to excite different fluorescent dyes on different particles. Longer wavelength lasers (e.g., greater than 750 nm) are known to those skilled in the art. A preferred laser excitation wavelength is about 785 nm. In a preferred, but not required aspect of the invention, a flow cytometry system with three lasers at 532, 650, and 780 nm is used.

Appropriate detectors 25 for detecting a particular emitting light 24 in the detection subsystem are known as will be understood by those with skill in the art with reference to this disclosure. The detectors can be photodiodes or photomultipliers or similar devices that convert light signals into electrical impulses thereby associating the detected light with its fluorescent source. Detectors for detecting forward and side scattered light are known to those in the art and can be used to detect light scatter in the detection system as will be understood by those with skill in the art with reference to this disclosure. Light scatter and fluorescence can be simultaneously detected with respect to each particle in the examination zone. In a preferred, but not required, aspect of the invention, a forward scatter detector, a side scatter detector, and photomultiplier tubes are employed in a detection subsystem. The detection subsystem can also employ a system of filters, mirrors, as well as other components advantageous in operating a cytometry device as will be understood by those with skill in the art with reference to this disclosure. The electrical signals from the detectors 26 are typically fed into the electronics of the system for signal and display processing, storage, and/or further processing.

In an analysis subsystem, hardware, such as a microprocessor 27 in combination with memory storage 28 such as a hard drive in a computer, collects detected data and processes the data. Suitable hardware used in the analysis system is known as will be understood by those with skill in the art with reference to this disclosure. The analysis system software, used for data and signal processing, can correlate detected data with known data to produce analytical results. The analysis subsystem can collect data from the electrical signals associated with each particle. A class of particles is established based on the common characteristics of the class of particles. The data from a known class of particles can be compared to the data detected from sample particles of an unknown class. The processed data and interpreted results can be given as output 29 to a user.

With reference to FIG. 3, a method according to the present invention comprises a first preprocessing phase. In the first preprocessing phase, various subpopulations of particles are prepared and coded 32, according to the present invention as described above, with different labels including multiple fluorescent labels and/or varying particle size. Each subpopulation of particles in a particular assay can then be preprocessed and baseline data for each particular subpopulation of particles can be collected to generate a set of functions for particle classification 33. In a second analytical phase, the particles are combined 34 and exposed to an analytical sample and any appropriate reagents 35. The particles are then analyzed and assigned to a particular subpopulation according to predetermined classifications 36. Measurements relating to each subpopulations analyte are accumulated. In a third interpretation phase, the accumulated data is processed 37 and the interpreted results are given as output to the user 38.

In the preprocessing phase, analyte specific particles are prepared containing the combination of fluorescent labels. The particle subpopulations are passed substantially one at a time through an examination zone in the flow cytometer. In the examination zone, an excitation laser at the appropriate excitation wavelength illuminates the particles. Baseline fluorescence data is collected for each subpopulation of particles. When size is used as an additional parameter for coding the particles, baseline data on the forward and side scatter for each subpopulation of particles is also collected.

In the analytical phase, the multiple subpopulations of particles are combined, to create a population of particles. The particles are allowed to react with an analytical sample along with any appropriate reagents employed in the particular assay panel. The particles are optionally washed and again passed substantially one at a time through the examination zone of the flow cytometer. In the examination. zone, the particles are illuminated by at least two excitation lasers at the appropriate excitation wavelengths. The excitation lasers may operate sequentially or substantially together. An advantage of the present invention is that because of the separation in wavelength between the fluorescent labels used to mark the particles and the fluorescent dyes used in analyte detection, spatial separation between the two excitation lasers in not needed.

The appropriate detectors measure the emissions signals from the excited particles. Fluorescence is detected in different channels for the fluorescent labels and fluorescent analyte dyes. When particle size is used as a parameter to distinguish between subpopulations of particles, forward scatter and side scatter particle signals are also detected.

In the interpretation phase, clusters of particles with similar fluorescence and forward and side scatter measurements are associated with analyte specificity by reference to the baseline fluorescence and scatter measurements made prior to combining the particles with the analyte. For each reaction and for each analyte-associated subpopulation of particles, a value is calculated that is equal to a statistic such as the median fluorescence from the fluorescence detection channel associated with the signal of that analyte. This produces a set of values for each reaction corresponding to each of the analytes in the assay panel. The relationship between the values and concentration of each analyte is determined using a curve fit based on the values from the reactions of previously prepared calibrator solutions. Each value-analyte concentration pair is fit to a four parameter logistic binding curve to determine curve parameters. The values measured from each of the test samples and the parameters determined from the curve fit are used to calculate the concentration of each analyte from each test sample.

Particles that have passed through the flow cytometer can be collected and sorted according to their classifications in different subpopulations.

EXAMPLES

Example 1

Cyanine Compounds Employed as Fluorescent Labels

Figure 4:
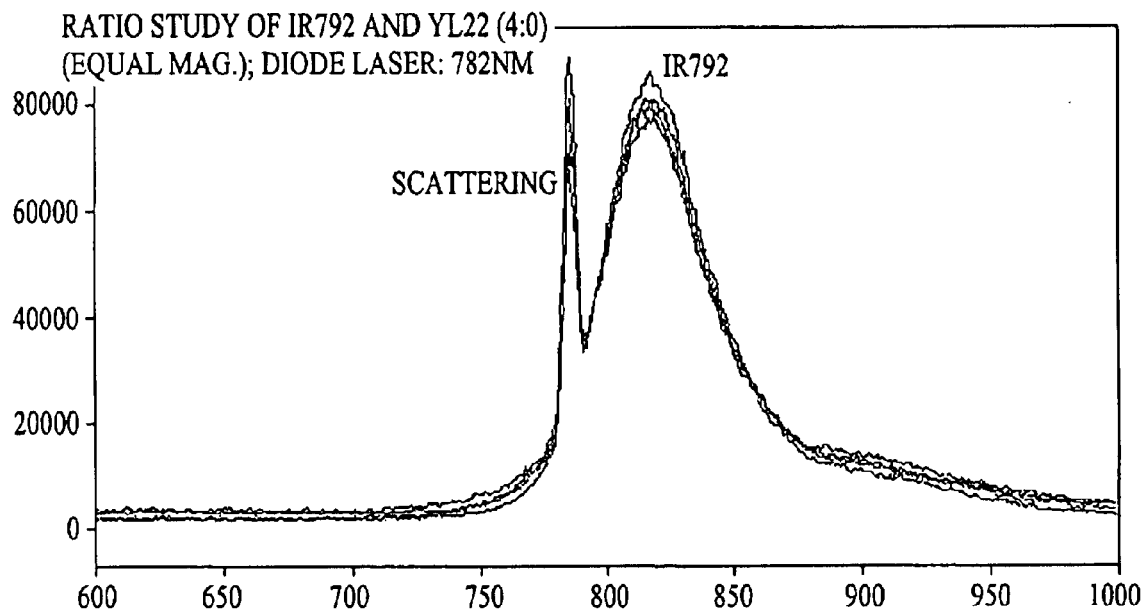
FIG. 4 is a graphical representation of a fluorescent emission stability study of an exemplary fluorescent label, IR 792, used in the particle detection system of the present invention.

IR-792 perchlorate, as shown below in Structure D, is a commercially available fluorescent label, useful in the present invention. IR-792 perchlorate, commercially available from Aldrich Chemical Company, is a fluorescent ring-locked cyanine compound that is excited by a 782 nm diode laser with a fluorescence emission frequency of 821 nm. The compound has good solubility in methylene chloride and stability in methylene chloride over time. FIG. 4, an overlay of the emission spectra of IR-792 perchlorate in methylene chloride for a two-month period, shows the stability of IR-792 perchlorate in solvent over time.

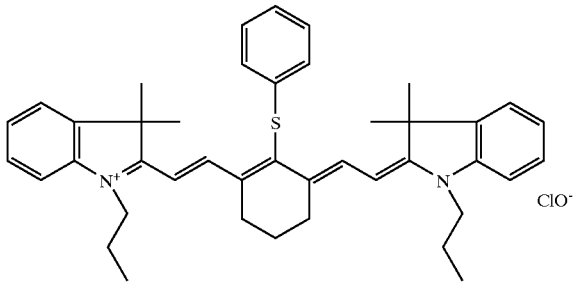

Structure D. IR 792 Perchlorate.

Figure 5:
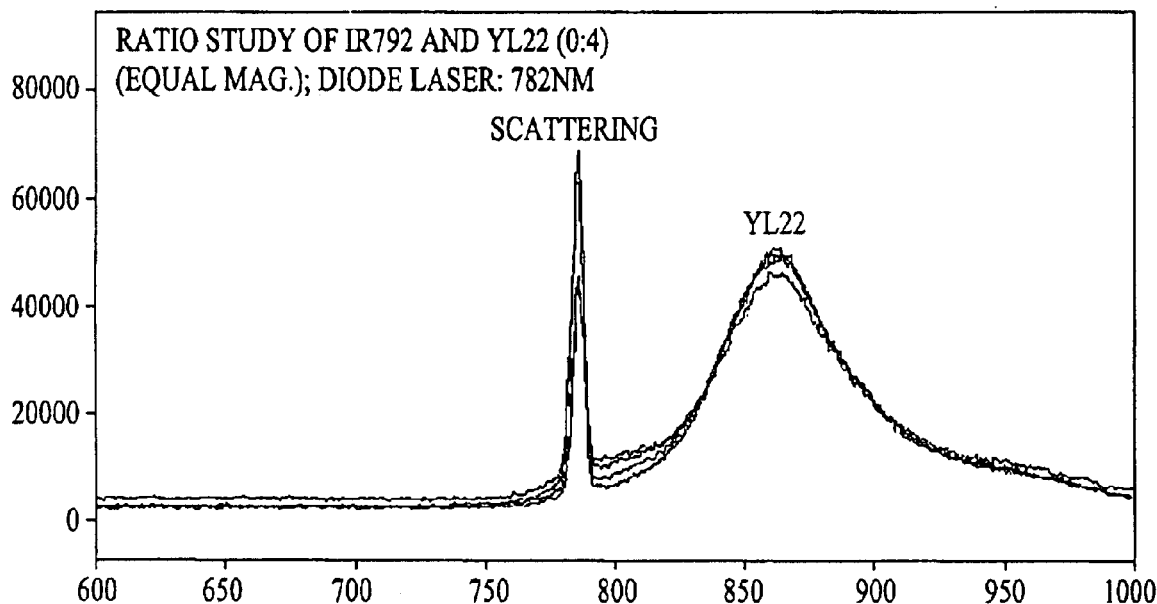
FIG. 5 is a graphical representation of a fluorescent emission stability study of an exemplary fluorescent label, Compound 6, used in the particle detection system of the present invention.

As an example of a pair of fluorescent labels used for particle coding, IR 792 perchlorate is incorporated in combination with Compound 6 according to the present invention. Compound 6 is excited by a 782 nm diode laser and has a fluorescence emission of 863 nm. Compound 6 has good solubility and stability in methylene chloride. FIG. 5, an overlay of the emission spectra of Compound 6 in methylene chloride for a two-month period, shows the stability of Compound 6 in solvent over time.

Figure 6:
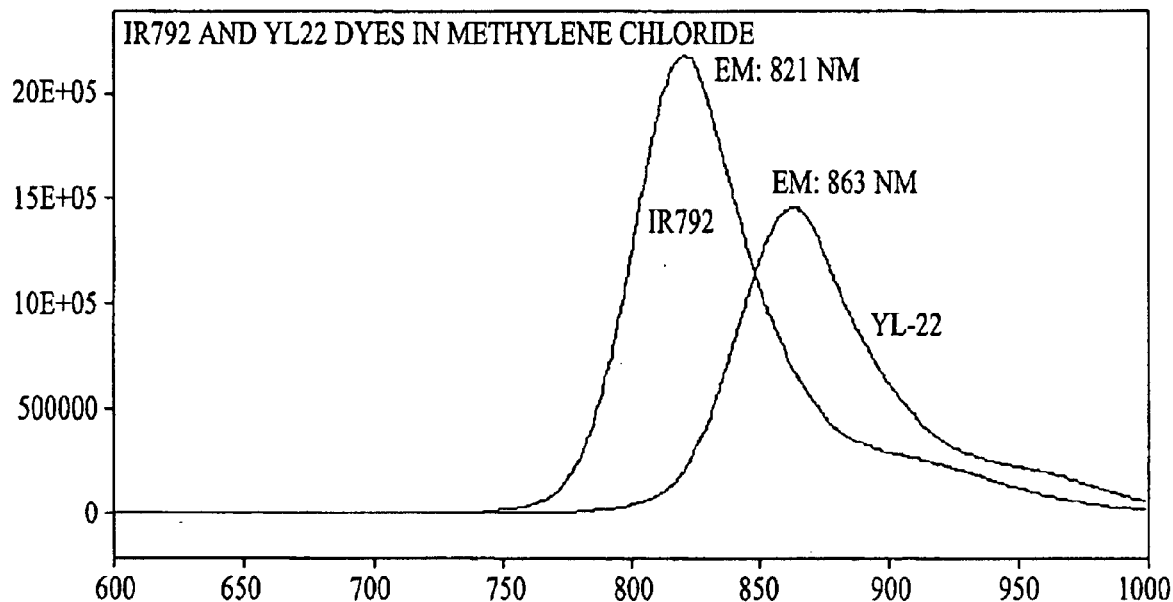
FIG. 6 is a graphical representation of the fluorescent emissions of an exemplary combination of fluorescent labels, IR 792 and Compound 6.
Figure 7:
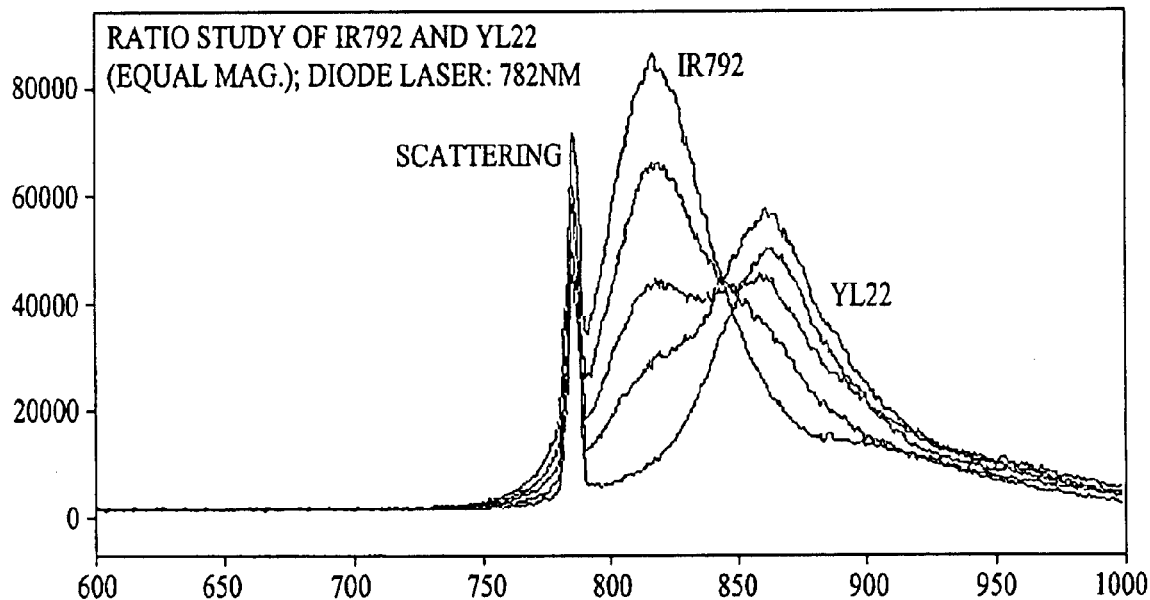
FIG. 7 is an overlay of the graphical representation of the fluorescent emissions of exemplary combinations of fluorescent labels, IR 792 and Compound 6, in varying ratios.
Figure 8:
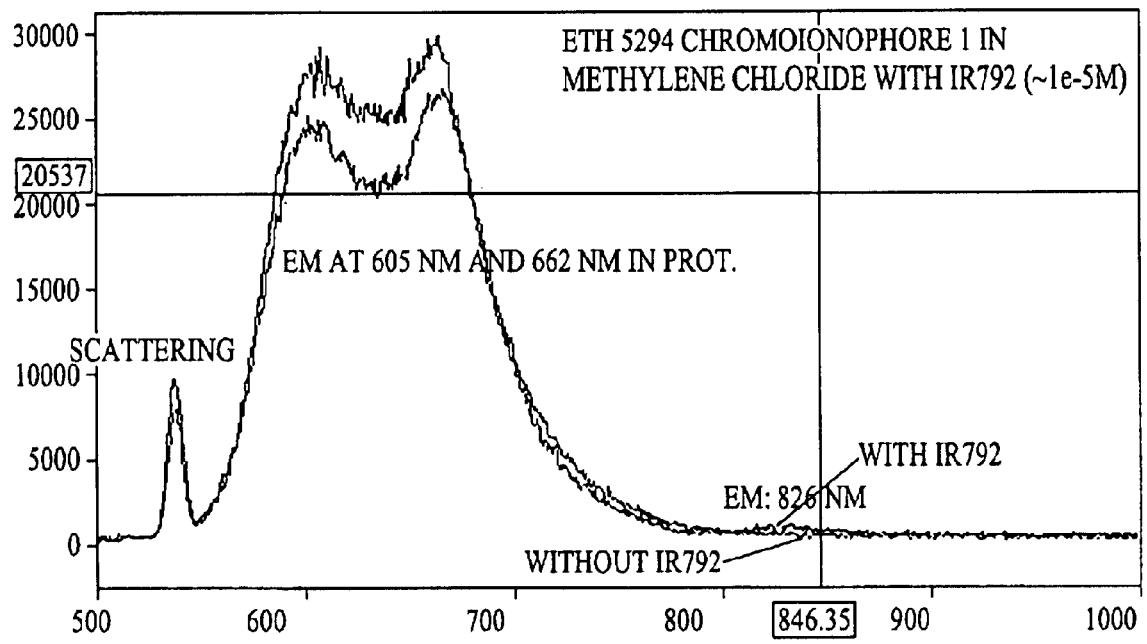
FIG. 8 is a graphical representation of the fluorescent emission of a combination of an exemplary fluorescent label, IR 792, and an exemplary analyte detection dye, ETH 5294, at the excitation wavelength of the analyte detection dye.
Figure 9:
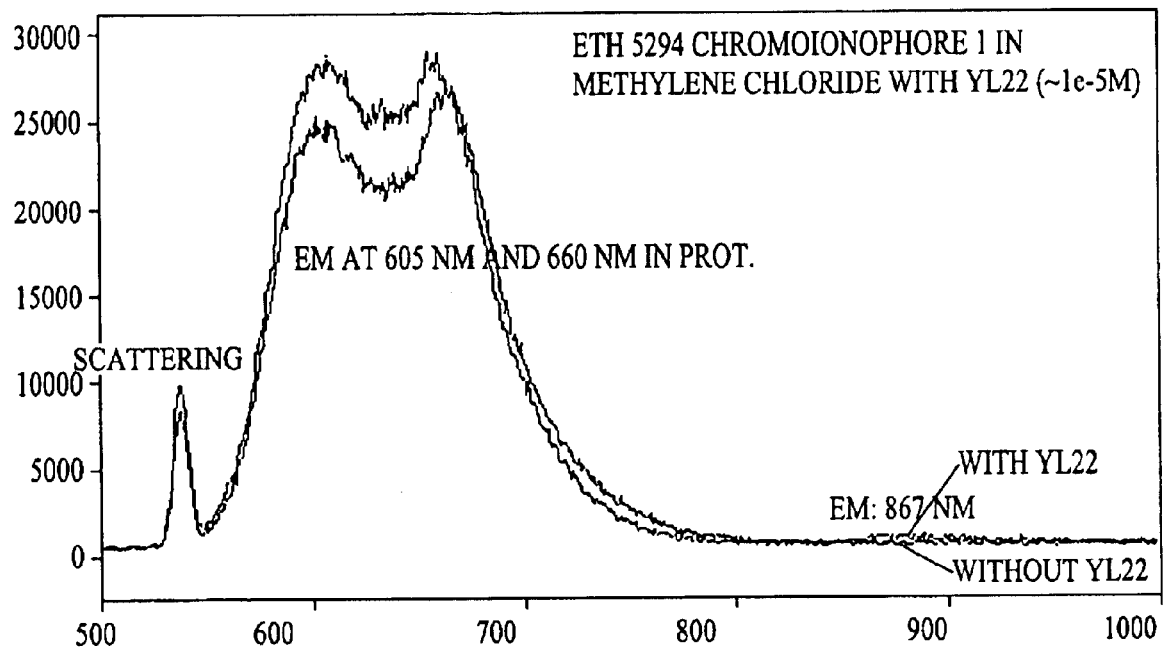
FIG. 9 is a graphical representation of the fluorescent emission of a combination of an exemplary fluorescent label, Compound 6, and an exemplary analyte detection dye ETH 5294, at the excitation wavelength of the analyte detection dye.

The pair of fluorescent labels is excited by the same frequency of exciting light. The emissions from the label pair are spectroscopically distinguishable such that the individual emissions of each label in a combined emissions spectrum will allow identification of the label pair according to relative intensity and emission wavelength. FIG. 6 shows the emission spectra of IR 792 perchlorate and Compound 6 in methylene chloride. The combination of fluorescent labels, according to the present invention, have negligible interaction with each other. FIG. 7 is an overlay of five emission spectra of different concentrations of IR 792 perchlorate and Compound 6. The relative ratios of IR 792 perchlorate and Compound 6 are: 4:0; 3:1; 2:2; 1:3; and 0:4, respectively. The iso-bar point observed in the emission spectra indicates null cross talk of the two fluorescent labels in methylene chloride. This is the basis of multiple combinations of fluorescers for coding particles. The fluorescent labels also have negligible interaction with fluorescent dyes employed in analyte detection as shown in FIG. 8, an overlay of the emission spectra of ETH 5294 with and without IR 792 perchlorate in methylene chloride at an excitation wavelength of 539 nm. FIG. 9 is an overlay of the emission spectra of ETH 5294 with and without Compound 6 in methylene chloride at an excitation wavelength of 539 nm. As seen in FIGS. 7 and 8, there is negligible spectral energy transfer from analyte dye, ETH 5294 to fluorescent labels, IR 792 perchlorate and Compound 6. Cross talk is minimal in IR 792 perchlorate and Compound 6, even at high concentration (e.g., $1 \times e^{-5}$ M).

TABLE 2

Summary of Spectral Data for IR-972 and Compound 6.

| Compound | $\lambda_{max}$ (methylene chloride) | Em. (methylene chloride) | Estimated Q.E. | $\epsilon$ | FWHM |
|---|---|---|---|---|---|
| IR 792 | 800 nm | 821 nm (Ex. 782 nm) | ~20% | 230K | ~50 nm |
| 6 | 838 nm | 863 nm (Ex. 782 nm) | ~15% | 210K | ~50 nm |

Example 2

Ring-Locked dibenzocyanine Compounds Used as Fluorescent Label Pairs

In another example, fluorescent Compounds 5a and 5b and Compounds 5c and 5d are employed in combination as fluorescent labels for coding particles. Compounds 5a–d are ring-locked dibenzocyanine compounds with a pair of extended alkane side chains. The label pairs differ by the inclusion or absence of a chlorine atom attached to the cyanine backbone above the locking ring. The alkane side chains increase the solubility of the charged labels in particle solvents and polymers and the stability of the labeled particles. Inclusion of the chlorine atom in the cyanine backbone causes the molecule to both absorb and emit at longer wavelengths than molecules that lack the chlorine atom. Table 3 summarizes the spectral data for Compounds 5a–d.

TABLE 3

Summary of Spectral Data for Compounds 5a–d.

| Compound | $\lambda_{max}$ (methylene chloride) | Em. (methylene chloride) |
|---|---|---|
| 5a | 787 nm | 833 nm (Ex. 782 nm) |
| 5b | 820 nm | 860 nm (Ex. 782 nm) |
| 5c | 787 nm | 833 nm (Ex. 782 nm) |
| 5d | 820 nm | 860 nm (Ex. 782 nm) |

Figure 10:
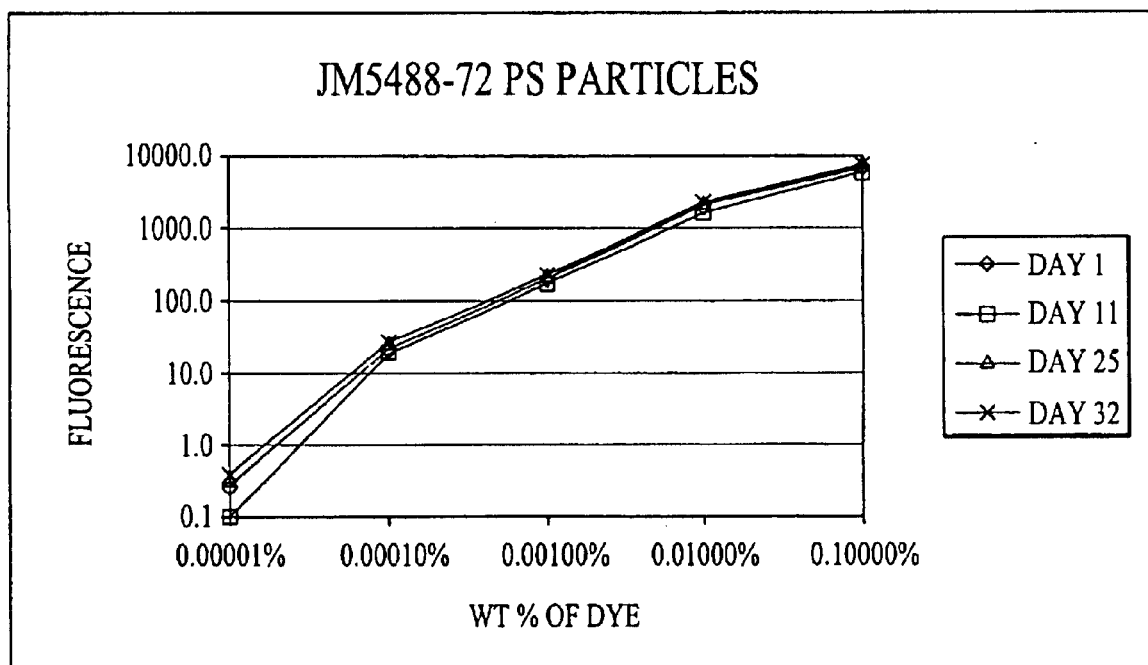
FIG. 10 is a graphical representation of a stability study using varying concentrations of an exemplary fluorescent label, Compound 5a, embedded in microparticles, over a 35 day period.
Figure 11:
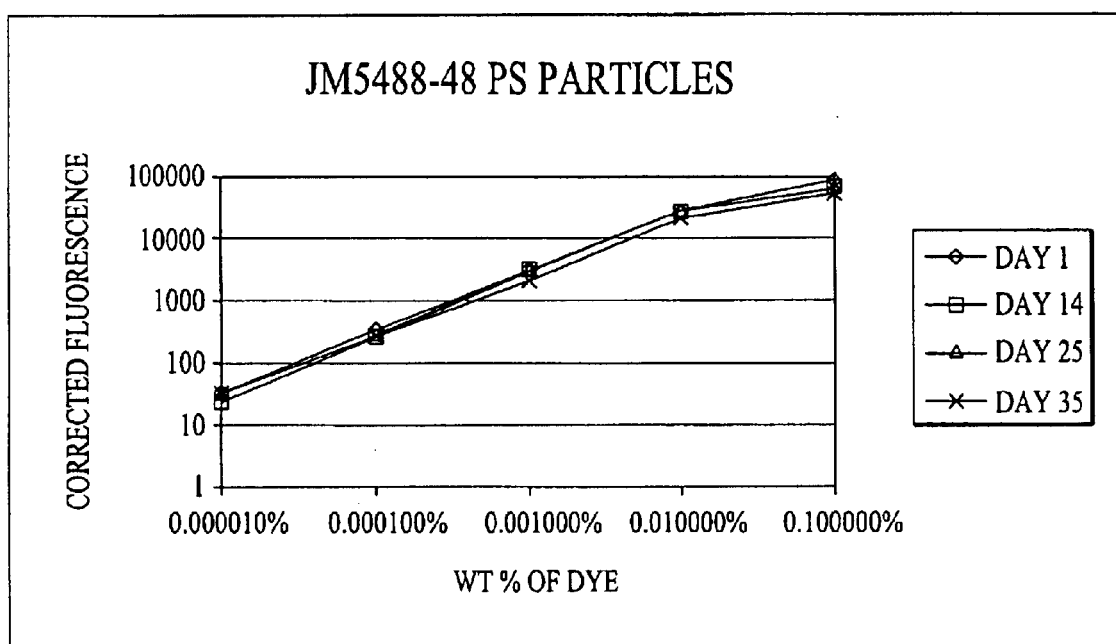
FIG. 11 is a graphical representation of a stability study using varying concentrations of an exemplary fluorescent label, Compound 5b, over a 35-day period.
Figure 12:
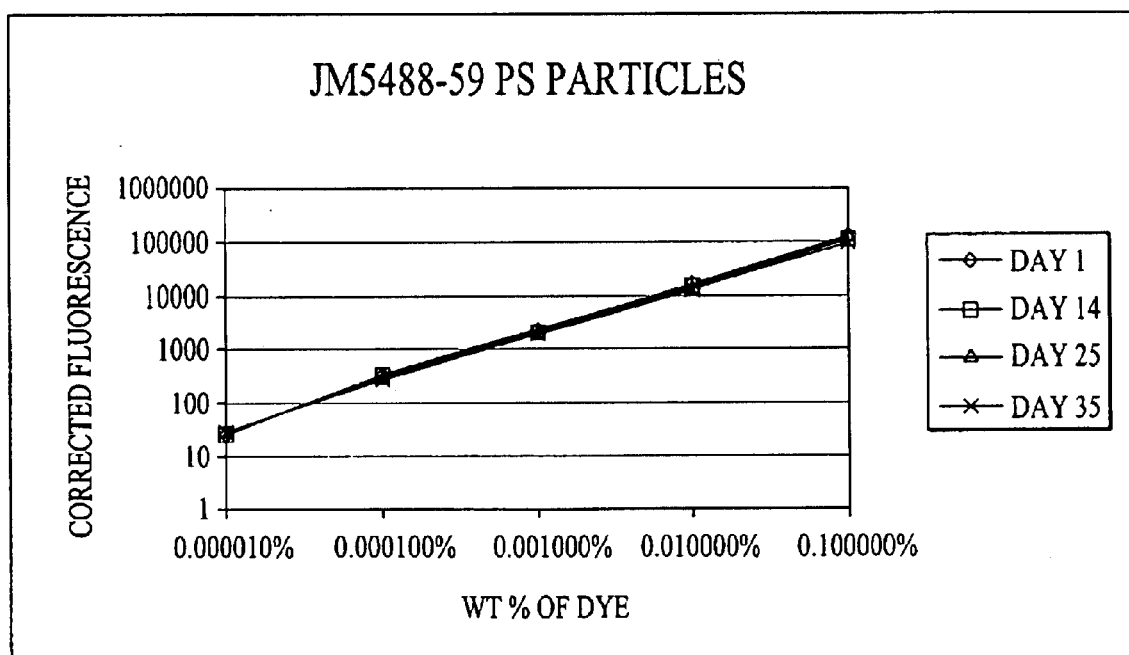
FIG. 12 is a graphical representation of a stability study using varying concentrations of an exemplary fluorescent label, Compound 5d, over a 35-day period.

FIG. 10, FIG. 11, and FIG. 12 show the fluorescence signal from particles incorporated with different concentrations of Compounds 5a, 5b, and 5d over time as measured in a flow cytometer with a 785 nm laser. The fluorescence emission spectra of Compounds 5a, 5b, and 5d, in accordance with the present invention, show increasing signal with increasing weight percentage of the fluorescent label as shown in FIG. 10, FIG. 11, and FIG. 12 and a lack of signal degradation over time.

Example 3

Preparation of Compound 6, [2-[2-[2-Phenylsulfyl-3-[(1,3-dihydro-3,3-dihydro-3,3-dimethyl -1-propl-2H-benzoindol-2-ylidene)ethylidene]-1-cyclohen-1-yl]ethenyl]3,3-dimethyl-1-propylbenzoindolium] Iodide Preparation of N-propyl-1,1,2-trimethyl-1H-benzyl indole iodide (2, R=$(CH_3)_2CH_3$). To a one-neck round bottom flask, equipped with stir bar, was charged with 1,1,2-trimethyl-1H-benzyl-indole (2 g, 9.6 mmole, 1) and iodopropane (2.4 g, 14.3 mmole). The flask was placed in an oil bath (pre-heated at 90° C.) for 24 hrs under $N_2$. The resulting reaction mixture was allowed to cool to ambient temperature and filtered. The solid was washed with iodopropane (5 mL), hexane (50 mL), and dried under vacuum at 60° C. for 6 hrs gave 3.2 g of a red colored solid in 88% yield. $^1$H NMR (CDCl$_3$) δ ppm: 1.15 (t, 3H), 1.88 (s, 6H), 2.08 (m, 2H), 3.21 (s, 3H), 4.79 (t, 2H), 7.67–7.74 (m, 2H), 7.82 (d, 1H), 8.04–8.13 (m, 3H). $^{13}$C NMR (CDCl$_3$) δ ppm: 11.29, 16.82, 21.62, 22.69, 51.44, 55.83, 112.54, 122.76, 127.55, 127.69, 128.58, 129.96, 131.38, 133.57, 136.99, 138.11, 195.28. TLC (9/1, CHCl$_3$/MeOH) $R_f$=0.43.

Preparation of [2-[2-[2-chloro-3-[(1,3-dihydro-3,3-dimethyl-1-propyl-2H-benzylindol-2-ylidene)ethylidene]-1cyclohexen-1-yl]ethenyl]-3,3-dimethyl-1-propylindolium] Iodide (5e). To a flame dried one-neck round bottom flask was dissolved N-propyl-1,1,2-trimethyl-1H-benzyl indole iodide (2 g, 5.3 mmole, 2) and N-[(3-(Anilinomethylene)-2-chloro-1-cyclohexen-1-yl)methylene]aniline (0.9 g, 2.6 mmole) (3b) in 50 mL of anhydrous ethanol under $N_2$. Sodium acetate (518 mg, 6.3 mmole) was added to the reaction solution and the resulting mixture was refluxed for 1 h. The reaction was cooled to ambient temperature and diluted with 10 mL of methanol. The solvent was evaporated under vacuum and the residue was purified by liquid chromatography on silica gel using mixture of methylene chloride and methanol as eluent to give 1.89 g of a dark green color solid in 43% yield after drying. $^1$H NMR (CDCl$_3$) δ ppm: 1.15 (t, 6H), 1.21 (t, 2H), 1.90–2.10 (m, 16H), 2.78 (t, 4H), 4.35 (t, 4H), 6.25 (d, 2H), 7.50 (m, 4H) 7.65 (t, 2H), 7.98 (m, 4H), 8.18 (d, 2H), 8.43 (d, 2H). $^{13}$C NMR (CDCl$_3$) δ ppm: 11.59, 20.69, 21.12, 26.67, 27.63, 46.46, 51.06, 65.78, 100.88, 110.89, 122.00, 125.08, 127.11, 127.72, 128.01, 130.08, 130.72, 131.83, 133.72, 139.66, 143.23, 149.76, 173.72. TLC (9/1, CHCl$_3$/MeOH) $R_f$=0.43.

Preparation of [2-[2-[2-Phenylsulfyl-3-[(1,3-dihydro-3,3-dihydro-3,3-dimethyl-1-propl-2H-benzoindol-2-ylidene) ethylidene]-1-cyclohen-1-yl]ethenyl]3,3-dimethyl-1-propylbenzoindolium]Iodide (6).

To a flame dried two-neck, 250-mL, round bottom flask was dissolved [2-[2-[2-chloro-3-[(1,3-dihydro-3,3-dimethyl-1-propyl-2H-benzylindol-2-ylidene)ethylidene]-1-cyclohexen-1-yl]ethenyl]-3,3-dimethyl-1-propylindolium iodide](500 mg, 0.65 mmole, 5e) in 100 mL of anhydrous DMF under $N_2$. Added sodium thiobenzene (1.7 g, 13.0 mmole) to the reaction solution and the resulting reaction mixture was stirred for 1 h at ambient temperature under $N_2$. The solvent was evaporated under high vacuum and the residue was purified by liquid chromatography on silica gel using mixture of methylene chloride and methanol as eluent to give 360 mg of a dark green color solid in 66% yield after drying. $^1$H NMR (CDCl$_3$) δ ppm: 1.08 (t, 6H), 1.78 (s, 12H), 1.92–2.07 (m, 4H), 2.09–2.11 (m, 2H), 2.82 (t, 4H), 4.26 (t, 4H), 6.26 (d, 2H), 7.28–7.30 (m, 5H), 7.41–7.48 (m, 4H), 7.58 (t, 2H), 7.91 (d, 4H), 8.04 (t, 2H), 8.78 (d, 2H). $^{13}$C NMR (CDCl$_3$) δ ppm: 11.60, 20.81, 21.12, 26.73, 27.39, 46.38, 50.90, 101.20, 110.81, 122.01, 124.97, 125.62, 126.04, 127.58, 128.00, 129.43, 130.04, 130.58, 131.75, 133.81, 133.94, 137.23, 139.66, 145.02, 150.50, 173.61. TLC (9/1, CHCl$_3$/MeOH) $R_f$=0.43. $\lambda_{max}$ (MeOH)=829 nm.

Example 4

Preparation of Compound 5a, [2[2[3[1,3-dihydro-3, 3-dimethyl-1-decyl-2H-benzoindol-2-ylidene) ethylidene]-1-cyclohexen-1-yl]ethenyl]3,3-dimethyl-1-decylbenzoindolium]Iodide Preparation of 2,3,3-Trimethyl-1-decyl-3-H-benzindolenium Iodide (2, R=(CH$_3$)$_9$CH$_3$). A mixture of 1,1,2-trimethyl-(1H)-benz[e]indole (1, 5.0 g., 23.89 mmol) and iododecane (20 mL, 95.46 mmol) was heated at 130° C. in an oil bath under Argon atmosphere with stirring overnight. The reaction mixture was cooled to ambient temperature and filtered. The product was washed with ether, and ethyl acetate (4×20 mL), and dried under vacuum to afford 7.42 g (64.9%) of pure product. TLC (5% MeOH/CH$_2$Cl$_2$):$R_f$=0.6.

Preparation of [2[2[3[1,3-dihydro-3,3-dimethyl-1-decyl-2H-benzoindol-2-ylidene)ethylidene]-1-cyclohexen-1-yl] ethenyl]3,3 -dimethyl-1-decylbenzoindolium]Iodide (5a). A solution of 1-decyl-2,3,3-trimethylbenzoindolinium Iodide (2, 600 mg., 1.25 mmol), N-[3-anilinomethylene)-1-cyclohexen-1-yl)methylene]aniline monochloride (3a, 206 mg, 0.67 mmol), and anhydrous Sodium acetate (200 mg, 2.4 mmol) in absolute ethanol (30 mL) was heated at reflux temperature under an Argon atmosphere overnight. The reaction mixture was cooled and the ethanol was removed under reduced pressure. The resulting crude product was purified by chromatography on silica gel using a methanol-CH$_2$Cl$_2$ gradient from 0% to 3%. The pure fractions were collected. The solvent was removed and the product was dried under Vacuum affording 430 mg (43%) of product. $R_f$ in 10% methanol in dichloromethane is 0.58, $\lambda_{max}$ 787 (MeOH). $^1$H (CDCl$_3$) δ 0.95 (t, 8H), 1.2–2.1 (45H0, 2.5 (t, 4H), 4.1 (t, 4H0, 6.1 (d, 2H), 7.3–7.6 (m, 6H) 7.9 (m, 6H), 8.2 (d, 2H).

Example 5

Preparation of Compound 5b, [2-[2-[2-Chloro-3-[(1, 3-dihydro-3,3-dimethyl-1-decyl-2H-benzoindol-2-ylidene)ethylidine]-1-cyclohexen-1-yl]ethenyl]3,3-dimethyl -1-decylbenzoindolium]Iodide The quarternary salt (2, R=(CH$_3$)$_9$CH$_3$), 1 g, 2.2 mmol) and 2-chloro-1-formyl-3-hydroxymethylene-cyclohoxene (4,193 mg, 1.1 mmol) were dissolved in a mixture of 1-butanol and bezene (7:3) in a flask equipped with a Dean-Stark trap. The mixture was heated under reflux with stirring overnight under Argon. The reaction was cooled to room temperature and the solvents were removed under vacuum. The residue was purified by column chromatography on silica gel using 3% methanol in dichloromethane. The fractions with absorption maxima at 820 were collected together. Removal of the solvent and drying under vacuum afforded pure dye 900 mg (45%). TLC (95:5 CH$_2$Cl$_2$/MeOH)$R_f$=0.33, VIS-NIR $\lambda_{max}$ 820 (MeOH). $^1$H NMR (CDCl$_3$) δ 0.95 (t, 8H), 1.3–2.1 (m, 44H0, 2.8 (t, 4H), 4.3 (t, 4H), 6.3 (d, 2H), 7.5 (m, 4H), 7.7 (t, 2H), 8.0 (m, 4H), 8.2 (d, 2H), 8.5 (d, 2H).

Example 6

Preparation of Compound 5c, [2[2-[3[(1,3-dihydro-3,3-dimethyl-1-octadecyl-2H-benzoindol -2ylidene) ethylidene]-1-cyclohexen-1yl]ethenyl]3,3-dimethyl-1-octadecylbenzoindolium]Iodide Preparation of 2,3,3-Trimethyl-1-Octadecyl-3H-benzindoleninum Iodide (2, R=(CH$_3$)$_{17}$CH$_3$). A mixture of 1,1,2-Trimethyl-1H-benzo(e)indole (1, 2.0g, 9.5 mmol) and iodooctadecane (4.18 g, 11 mmol) was heated at 130° C. in an oil bath with stirring overnight. On cooling, the product was extracted with methanol and evaporated. Chromatography of the residue on silica gel column eluted with 0% to 5% methanol in dichloromethane gradient furnished the pure product. After solvent removal and vacuum drying 2.3 g (41%) of pure product was obtained. TLC (90:10 $CH_2Cl_2$/MeOH)$R_f$=0.55.

[2[2-[3[(1,3-dihydro-3,3-dimethyl-1-octadecyl-2H-benzoindol-2ylidene)ethylidene]-1-cyclohexen-1yl]ethenyl] 3,3-dimethyl-1octadecylbenzoindolium]Iodide (5c). A solution of 1-octadecyl-2,3,3-trimethylbenzoindolinium Iodide (2,565 mg, 0.958 mmol), N-[3-anilinomethyelene)-1-cyclohexen-1yl)methylene]aniline monochloride (3,156 mg, 0.48 mmol), and Sodium acetate (150 mg, 1.8 mmol) in absolute ethanol (30 mL) were heated at reflux temperature under an Argon atmosphere overnight. The reaction was cooled and the ethanol was removed on a rotary evaporator. The residue was chromatographed on silica gel column using dichloromethane then 5% methanol in $CH_2Cl_2$. The pure fractions were pooled together and the solvent was evaporated to give 440 mg (40%), of deep green solid. $R_f$=0.64 (10% methanol in dichloromethane), λmax 787 (MeOH). $^1$H NMR ($CDCl_3$) δ 0.95 (t, 8H), 1.2–2.1 (m, 76H), 2.8 (t, 4H), 4.3 (t, 4H), 6.3 (d, 2H), 7.5–8.5 (m, 14H).

Example 7

Preparation of 5d, [2-[2-[2-Chloro-3-[(1,3-dihydro-3,3-dimethyl-1-octdecyl-2H -benzoindol-2-ylidene) ethylidene]-1cyclohexen-1-yl]ethenyl]3,3-dimethyl-1-ocdecylbenzoindolium]Iodide The quarternary salt (2, R=($CH_3$)$_{17}CH_3$), 1.4 g, 2.4 mmol), and 2-chloro-1-formyl-3-hydroxymethylene-cyclohexene (3,220 mg, 1.2 mmol) were dissolved in a mixture of 1-butanol and benzene (7:3) in a flask equipped with a Dean-Stark trap. The mixture was heated at reflux with stirring overnight under Argon. The reaction was cooled to room temperature and the solvents were removed in Vacuum. The residue was purified by column chromatography on silica gel using 3% methanol in dichloromethane. The fractions with absorption maxima at 820 were collected. Removal of solvent and drying under vacuum afforded 1.1 g (40%) of pure chloro dye. TLC (5% dichloromethane) $R_f$=0.38, VIS-NIR $λ_{max}$ 820 nm in methanol. $^1$H NMR ($CDCl_3$) δ 0.9 (t, 8H), 1–3–2.0 (m, 76H, 2.8 (t, 4H), 4.3 (t, 4H), 6.3 (d, 2H0, 7.5 (m, 4H), 7.7 (t, 2H), 8.0 (m, 4H), 8.2 (d, 2H), 8.5 (d, 2H).

Example 8

Incorporation of Fluorescent Labels into Particles. General Swell-Shrink Method

Figure 13:
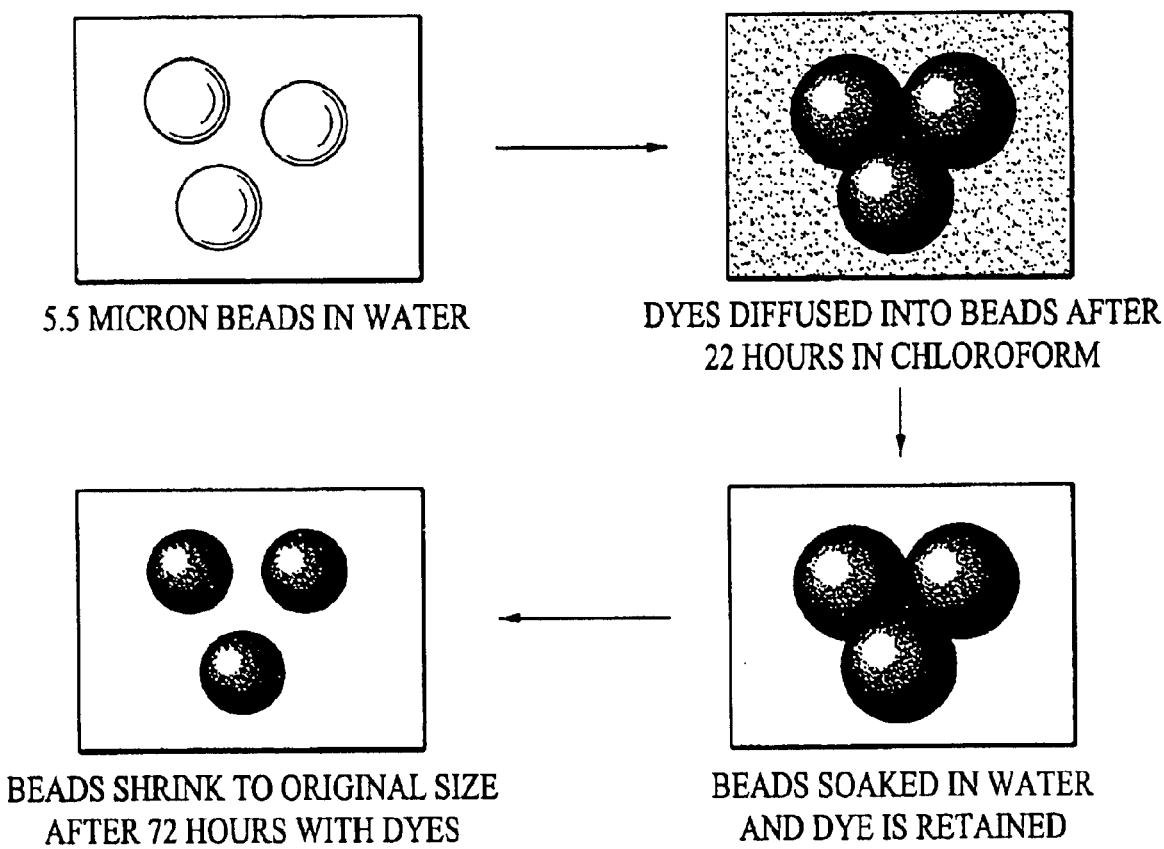
FIG. 13 is an illustration of an exemplary process for incorporating dyes into beads.

A bead dyeing process useful in the present invention is illustrated in FIG. 13. A set of 5.5 micron beads in water, purchased from Bangs Labs, Inc. are mixed with known proportions of dyes, dissolved in chloroform. The beads swell to about 7 microns in 22 hours and the dyes diffuse into the beads. The beads are then soaked in water and the dyes are retained in the beads. The beads shrink back to their original 5.5 micron size after 72 hours, incorporating the known proportions of dyes within the beads.

Example 9

Fluorescent Bead Labeling. General Procedure

Step 1. Preparation of Bead Suspension (In a 5-mL Vial w/Teflon Lined Cap). Bead suspensions of 10 μL for 5.5 μm beads (1.0E+07 beads), 10 μL for 10.2 μm beads (1.7E+06 beads), and 4 μL for 4.45 μm beads (7.9E+06 beads) were prepared using an aqueous buffer containing surfactants and preservatives ("aqueous buffer") (1 mL), water (1.2 mL), and ethanol (0.5 mL). The bead suspensions were heated in an oil bath at 70° C. (+/−2° C.) for 20 min.

Step 2. Preparation of Dye Solution. Dyes, according to the present invention, (125 μL, in $CHCl_3$) were dissolved in ethanol (500 μL), and methylene chloride (12.5 μL).

Step 3. Labeling Beads. To 50 μL (20 μL for 4.45 μm) of the dye solution from Step 2 was added to the bead suspension prepared according to Step 1. The suspension was heated and stirred at 70° C. (+/−2° C.) for 3 hours in an oil bath. The tube was uncapped and vented for 1 hour and cooled to room temperature.

Step 4. Washing. The suspension from step 3 was centrifuged and the supernatant was removed. The beads were washed three times with aqueous buffer (2 mL) and water (8 to 10 mL).

Dye Loading Procedure.

The following standard dye stock solutions of Compounds 5a and 6 were prepared as follows. Compound 5a: 2 mg in 2.5 mL chloroform ($10^{-3}$ M); 10 mg in 1.25 mL chloroform ($10^{-2}$ M). Compound 6 2.1 mg in 2.5 mL chloroform ($10^{-3}$ M); 8.4 mg in 1.25 mL chloroform ($10^{-2}$ M). Dye solutions according to Table 4, were then prepared from ethanol (500 μL Beckman, 200 proof), methylene chloride (12.5 μL, JTB 30812), Compound 5a (X μL, from Table 4), Compound 6 (Y μL, from Table 4), and chloroform (Z μL, from Table 4, Mallinkrodt, 4440).

To 5-mL vials equipped with stir bars and Teflon caps, 1.00 mL of aqueous buffer, 0.5 mL of Ethanol (Beckman, 200 proof), 1.2 mL of water and 10 μL of polymer based beads (5.5 μm, Bangs Labs. Cat# PC06N, Lot# 2820) were added. The vials were then placed in an oil bath preheated to 70° C. +/−2° C. After heating the bead solution for about 20 min, 50 μL of dye solution was added to each vial. The vials were then placed in an oil bath and incubated for 3 hours at 70° C. (+/−2° C). The organic solvents were then removed by removing the caps from the caps from the vials followed by continued heating of the vial. for 1 hour. The dye solution was then cooled and the solution in each vial was transferred to a 15-mL PP centrifuge tube using 1.5 mL of water to rinse the vial. The tubes were centrifuged for 10 min at 2420 rpm on a Beckman GS-6R with a GH-3.7 rotor.

After centrifugation, the supernatant was removed from the tubes. Aqueous buffer (2 mL and water (8 mL) were added to the tube. The tube was then vortexed, sonicated for 5 min, and centrifuged for 10 min at 2420 rpm to obtain colored pellet. The supernatant was removed after centrifuging. The above step was repeated 3 times and the final volume was adjusted to 2 mL with the aqueous buffer.

TABLE 4

| Sample # | Compound 5a X | Compound 6 Y | $CHCl_3$ (μL) Z |
|---|---|---|---|
| 1 | 1 μL $10^{-3}$ M | 5 μL $10^{-3}$ M | 119 |
| 2 | 1 μL $10^{-3}$ M | 20 μL $10^{-3}$ M | 104 |
| 3 | 1 μL $10^{-3}$ M | 40 μL $10^{-3}$ M | 84 |
| 4 | 0 | 80 μL $10^{-3}$ M | 40 |
| 5 | 4 μL $10^{-3}$ M | 0 | 121 |
| 6 | 3 μL $10^{-3}$ M | 5 μL $10^{-3}$ M | 117 |
| 7 | 4 μL $10^{-3}$ M | 20 μL $10^{-3}$ M | 101 |
| 8 | 4 μL $10^{-3}$ M | 40 μL $10^{-3}$ M | 81 |
| 9 | 1 μL $10^{-3}$ M | 80 μL $10^{-3}$ M | 44 |
| 10 | 0 | 12 μL $10^{-2}$ M | 113 |
| 11 | 4 μL $10^{-3}$ M | 5 μL $10^{-3}$ M | 116 |
| 12 | 8 μL $10^{-3}$ M | 20 μL $10^{-3}$ M | 97 |
| 13 | 8 μL $10^{-3}$ M | 40 μL $10^{-3}$ M | 77 |
| 14 | 8 μL $10^{-3}$ M | 10 μL $10^{-2}$ M | 107 |
| 15 | 8 μL $10^{-3}$ M | 0 | 117 |
| 16 | 8 μL $10^{-3}$ M | 10 μL $10^{-3}$ M | 107 |

TABLE 4-continued

| Sample # | Compound 5a X | Compound 6 Y | CHCl$_3$ (µL) Z |
|---|---|---|---|
| 17 | 16 µL 10$^{-3}$ M | 40 µL 10$^{-3}$ M | 69 |
| 18 | 16 µL 10$^{-3}$ M | 80 µL 10$^{-3}$ M | 29 |
| 19 | 16 µL 10$^{-3}$ M | 10 µL 10$^{-3}$ M | 99 |
| 20 | 32 µL 10$^{-3}$ M | 40 µL 10$^{-3}$ M | 53 |
| 21 | 32 µL 10$^{-3}$ M | 10 µL 10$^{-2}$ M | 83 |
| 22 | 16 µL 10$^{-3}$ M | 0 | 108 |
| 23 | 64 µL 10$^{-3}$ M | 0 | 61 |
| 24 | 48 µL 10$^{-3}$ M | 40 µL 10$^{-3}$ M | 37 |
| 25 | 32 µL 10$^{-3}$ M | 10 µL 10$^{-3}$ M | 83 |
| 26 | 64 µL 10$^{-3}$ M | 40 µL 10$^{-3}$ M | 21 |
| 27 | 64 µL 10$^{-3}$ M | 8 µL 10$^{-2}$ M | 53 |
| 28 | 74 µL 10$^{-3}$ M | 5 µL 10$^{-2}$ M | 46 |
| 29 | 80 µL 10$^{-3}$ M | 0 | 45 |
| 30 | 125 µL 10$^{-3}$ M | 0 | 0 |

Example 10

Preparation of Oligonucleotide Coupled Fluorescently Labeled Beads

The experimental procedure below describes the procedure for covalently coupling oligonucleotides to the surface carboxyl groups to fluorescently labeled beads. In Example 10, 5.5 micron Bangs beads were used and the beads were fluorescently labeled according to the procedure described in Experiment 9. The number of ligands per bead were determined by hybridizing a dye-labeled oligonucleotide to a coupled oligonucleotide and measuring the intensity of its fluorescence by cytometry. In the experimental procedure described below, an accurate measurement of 500,000 beads, coupled in each of two duplicate reactions, can be obtained. The carboxyl groups on the beads were assumed to have a parking area (Certificate of Analysis, Bangs Laboratories, Inc.) of 82.3 square Angstroms (i.e., there are approximately 100,000,000 carboxyl groups per bead).

In the procedures described below, suspensions of beads are typically vortexed (V) for 5 seconds, sonicated (S) for 5 minutes and centrifuged (C) for 5 minutes at 14,000 revs per minute (rpm).

EDC (1-Ethyl-3-(3-Dimethylaminopropyl)carbodiimide Hydrochloride, Pierce, P/N 22980), stored at freezing temperature in a desiccant containing container, was removed from freezing (storage) temperature and warmed to room temperature while remaining in the container with the desiccant.

A bead stock solution was created at a bead concentration of approx. 62,500 beads/µL. The bead stock solution was vortexed (V) and sonicated (S). Bead stock solution (8 µL) was added to a labeled 0.65 mL Microfuge™ tube (Bioexpress, #C-3259-1). MES buffer (8 µL, 1.0 M, pH 4.7) was added to the 8 µL bead stock solution followed by vortexing and sonication. The final volume of the solution was 16 µL. The bead stock solution was equilibrated at room temperature for 3–20 hours.

After equilibration, coupling oligonucleotide (2.0 µL at 100.0 pmoles/µL in distilled deionized (DI) water) and MES buffer (2.0 µL, 1.0M, pH 4.7) was added to the Microfuge™ tube. The tube was vortexed and sonicated according to standard procedure. The final solution contained approximately 500,000 beads coupled to oligonucleotide in a 20.0 µL solution.

Three 1.7 mL Microfuge™ tubes (Bioexpress, #C-3260-1) were labeled A, B, and C. EDC (approximately 10 mg, Pierce, P/N 22980) was added to each tube. The weight of EDC in each tube was noted and the tubes were capped.

To the first tube, tube A, enough DI water. was added to create a 10 mg/150 µL concentration solution. The tube was vortexed to dissolve the EDC. The EDC solution from tube A (1.7 uL) was immediately added to the oligonucleotide coupled bead solution. The tube of oligonucleotide coupled beads containing EDC was then vortexed and sonicated according to standard procedure followed by incubation at room temperature for fifteen minutes after sonication.

To the second tube, tube B, enough DI water was added to create a 10 mg/150 µL concentration solution. The tube was then vortexed to dissolve the EDC. The EDC solution from tube B (1.7 µL) was immediately added the bead solution from tube A ("reaction tube"). The reaction tube was then vortexed, sonicated, and incubated at room temperature for fifteen minutes after sonication.

To the third tube, tube C, enough DI water was added to create a 10 mg/150 µL concentration solution. Tube C was then vortexed to dissolve the EDC. The EDC solution from tube C (1.7 uL) was immediately added to the reaction tube from above. The reaction tube was then vortexed, sonicated, and incubated at room temperature for fifteen minutes after sonication.

After the 15 minutes from the above sonication, 500 uL of a 1×PBS/0.02% Tween20™ (Sigma) solution was added to the reaction tube. The reaction tube was then vortexed, sonicated and centrifuged.

After centrifugation, the supernatant was carefully removed from each tube using a P200 Pipetteman™ with a "loading" tip. The pellet of beads on the bottom of the containers was not disturbed. Recentrifugation of the sample is required when the bead pellet is disturbed.

Tween20™ solution (500 uL 2×SSC/0.02% Tween20™, Sigma) was added to each reaction tube. The tubes were then vortexed, sonicated and centrifuged. The supernatant from each tube was carefully removed using a P200 Pipetteman™ with a "loading" tip (Bioexpress P-3207-2). The pellet of beads on the bottom of the container was not disturbed; otherwise requiring recentrifugation.

Tween20™ solution (100 uL of 2×SSC/0.02% Tween20™, Sigma) solution was added to each tube. The tubes were then vortexed, and sonicated. Each suspension contained approximately 5,000 coupled beads per µL. According to calculations, coupled beads were stored at 4° C. at this point.

Example 11

Hybridization of Labeled Oligonucleotides to Bead-Coupled Oligonucleotides

The following hybridizations were done in duplicate for each of the two batches of coupled beads obtained above.

An oligonucleotide hybridization solution was prepared by adding 15 µL of 5M NaCl and 10 µL of 1 pmole/µL (in DI water) hybridizing oligonucleotide to a 0.65 mL Microfuge™ tube followed by 65 µL DI water to a final volume of 90 µL. The tube was then vortexed and 18 µL of the solution in the tube was pipetted into a PCR tube.

Oligonucleotide coupled beads, prepared as described above, were vortexed and sonicated. To a Microfuge™ tube, 2 uL of oligonucleotide coupled beads (at approx. 5000 beads per uL,) were added to the 18 µL hybridization solution (final volume will be 20 uL the PCR tube; Bioexpress 3412).The tube was then vortexed. The "Hyb30minutes" program was run for the PCR tube in the thermocycler. Tween20™ solution (50 µL, 2×SSC/0.02%

Tween20™, Sigma) was added to each PCR tube. The tube was then vortexed and the entire contents were then transferred to cytometry tube containing 230 μL of 2×SSC/0.02% Tween20™. The cytometry tubes were then vortexed, sonicated, and analyzed by flow cytometry.

Example 12

Bead-Based Cytokine Assay

A solution of oligonucleotide coupled fluorescently labeled beads were prepared according to Example 10. The beads were, vortexed and sonicated for 5 minutes using a bath sonicator.

Oligonucleotide-Monoclonal antibody (oligo-Mab) conjugated bead samples were prepared by adding 18 μL of Casein Blocker in a standard diluent solution of TBS in 0.15 M NaCl ("diluent"), 1 μL of 300 ng/μL oligo-Mab conjugate (300 ng), and 1 μL of fluorescently labeled beads (approximately 10,000 beads) to a 0.65 mL tube and vortexing.

The beads were then hybridized for 30 minutes at 45° C. using a thermal cycler.

Appropriate concentrations of cytokine standards, in the range of 10,000 to 1 pg/mL, were then prepared by diluting cytokine stock into the diluent. After hybridization in the thermal cycler, the tubes were removed from the thermal cycler and 150 μL of diluent was added to each tube. The tubes were then vortexed and centrifuged for 10 minutes at 14,000 rpm. After vortexing, the supernatant was carefully removed from each tube. Diluted cytokine standards (20 μL) were added to appropriate tubes containing hybridized beads. The tubes were then vortexed until the bead pellet was resuspended.

After incubating the tubes in a heat block set at 37° C. for one hour, 150 μL of diluent was added to each tube. The tube was then vortexed and centrifuged for 10 minutes at 14,000 rpm. The supernatant was carefully removed from each tube and 20 μL of 1.25 ng/μL biotinylated secondary antibody (25 ng) was added to each tube. The tube was then vortexed until the bead pellet was resuspended followed by incubation in a heat block set at 37° C. for one hour.

After incubation, 150 μL of diluent was added to each tube containing secondary antibody. The tubes were then vortexed and centrifuged for 10 minutes at 14,000 rpm. The supernatant was carefully removed from each tube and 20 μL of 25 ng/μl streptavidin-PBXL (500 ng) was added to each tube. The tube was then vortexed until the bead pellet was resuspended followed by incubation in a heat block set at 37° C. for one hour.

After incubation, 50 μL of diluent was added to each tube and the tube was vortexed. Each standard was transferred to a cytometry test tube containing 20 μL of diluent and the samples were read by flow cytometry.

Test samples were prepared according to the above procedure, substituting test samples for the cytokine standard solutions and read by flow cytometry.

What is claimed is:

1. A use of a fluorescent label in a particle comprising incorporating one or more fluorescent label into a particle, at least one fluorescent label being a compound of the formula:

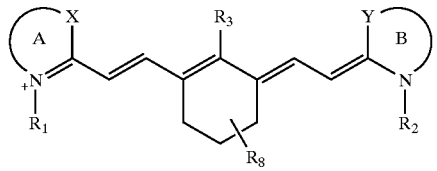

wherein:

A and B each independently represent ring structures with sufficient carbon atoms to make up a cyanine nuclei;

X and Y are each independently selected from the group consisting of O, S, $NR_9$, and $CR_9R_{10}$;

$R_1$ and $R_2$ are each independently selected from the group consisting of H, $C_1$–$C_{20}$ alkyl, $C_1$–$C_{20}$ haloalkyl, $C_1$–$C_{20}$ alkylene, and $C_1$–$C_{20}$ haloalkylene;

$R_3$ is selected from the group consisting of H, halogen, OH, $OR_{11}$, $SR_{11}$, $NR_{11}R_{12}$, $C_1$–$C_6$ alkyl, $C_1$–$C_6$ alkylene, $C_3$–$C_6$ cycloalkyl, $C_3$–$C_6$ cycloheteroalkyl, $C_3$–$C_6$ cycloalkylene, $C_3$–$C_6$ cycloheteroalkylene, phenyl, biaryl, heteroaryl, and heterobiaryl, wherein the $C_1$–$C_6$ alkyl, $C_1$–$C_6$ alkylene, $C_3$–$C_6$ cycloalkyl, $C_3$–$C_6$ cycloheteroalkyl, $C_3$–$C_6$ cycloalkylene, $C_3$–$C_6$ cycloheteroalkylene, phenyl, biaryl, heteroaryl and heterobiaryl groups are unsubstituted or substituted with halogen, OH, $C_1$–$C_4$ alkyl, or $C_1$–$C_4$ haloalkyl;

$R_8$ is selected from the group consisting of $C_1$–$C_4$ alkyl, and $C_1$–$C_4$ haloalkyl;

$R_9$ and $R_{10}$ are each independently selected from the group consisting of hydrogen, $C_1$–$C_4$ alkyl, and $C_1$–$C_4$ haloalkyl; and $R_{11}$ and $R_{12}$ are each independently selected from the group consisting of $C_1$–$C_6$ alkyl, $C_3$–$C_6$ cycloalkyl, phenyl, biaryl, heteroaryl, or heterobiaryl, wherein the $C_1$–$C_6$ alky$_1$, $C_1$–$C_6$ cycloalkyl, phenyl, biaryl, hereroaryl, and heterobiaryl groups are unsubstituted or substituted with halogen, OH, $C_1$–$C_4$ alkyl, or $C_1$–$C_4$ haloalkyl, or when $R_3$ represents $NR_{11}R_{12}$, $R_{11}$ and $R_{12}$ may be taken together to form an optionally substituted $C_3$–$C_6$ aliphatic or $C_3$–$C_6$ aromatic heterocyclic ring.

2. The use of a fluorescent label according to claim 1, wherein at least one fluorescent label is a compound of the formula:

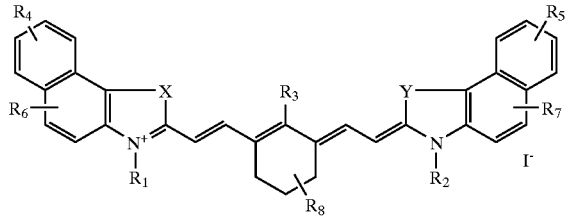

wherein:

$R_4$, $R_5$, $R_6$, and $R_7$ are each independently selected from the group consisting of hydrogen, halogen, OH, $C_1$–$C_4$ alkyl, or $C_1$–$C_4$ haloalkyl, phenyl, and heteroaryl.

3. The use of a fluoresecut label according to claim 2 wherein $R_1$ and $R_2$ are identical.

4. The use of a fluorescent label according to claim 3, wherein at least one fluorescent label is a compound of the formula:

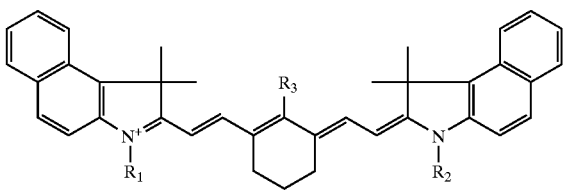

wherein:
  $R_1$ and $R_2$ are each independently a $C_1$–$C_{20}$ alkyl; and
  $R_3$ is H, halogen, or —S—phenyl.

5. The use of a fluorescent label according to claim 1 wherein the ring structures represented by A and B are each independently a benzoindole ring.

6. The use of a fluorescent label according to claim 1 wherein each fluorescent label has a near-infrared excitation wavelength.

7. The use of a fluorescent label according to claim 1 wherein each fluorescent label has an emitting light greater than 750 nm.

8. A method for incorporating a fluorescent label into a particle comprising:
  a) preparing a suspension of particles; and
  b) adding a solution of two or more fluorescent labels to the suspension, thereby incorporating the fluorescent labels into the particles, where at least one fluorescent label is a compound of the formula:

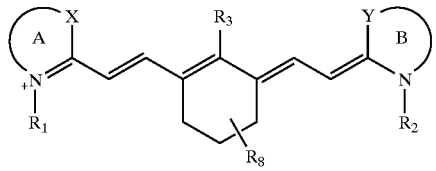

wherein:
  A and B each independently represent ring structures with sufficient carbon atoms to make up a cyanine nuclei;
  X and Y are each independently selected from the group consisting of O, S, $NR_9$, and $CR_9R_{10}$;
  $R_1$ and $R_2$ are each independently selected from the group consisting of H, $C_1$–$C_{20}$ alkyl, $C_1$–$C_{20}$ haloalkyl, $C_1$–$C_{20}$ alkylene, and $C_1$–$C_{20}$ haloalkylene;
  $R_3$ is selected from the group consisting of H, halogen, OH, $OR_{11}$, $SR_{11}$, $NR_{11}R_{12}$, $C_1$–$C_6$ alkyl, $C_1$–$C_6$ alkylene, $C_3$–$C_6$ cycloalkyl, $C_3$–$C_6$ cycloheteroalkyl, $C_3$–$C_6$ cycloalkylene, $C_3$–$C_6$ cycloheteroalkylene, phenyl, biaryl, heteroaryl, and heterobiaryl, wherein the $C_1$–$C_6$ alkyl, $C_1$–$C_6$ alkylene, $C_3$–$C_6$ cycloalkyl, $C_3$–$C_6$ cycloheteroalkyl, $C_3$–$C_6$ cycloalkylene, $C_3$–$C_6$ cycloheteroalkylene, phenyl, biaryl, heteroaryl and heterobiaryl groups are unsubstituted or substituted with halogen, OH, $C_1$–$C_4$ alkyl, or $C_1$–$C_4$ haloalkyl;
  $R_8$ is selected from the group consisting of $C_1$–$C_4$ alkyl, and $C_1$–$C_4$ haloalkyl;
  $R_9$ and $R_{10}$ are each independently selected from the group consisting of hydrogen, $C_1$–$C_4$ alkyl, and $C_1$–$C_4$ haloalkyl; and
  $R_{11}$ and $R_{12}$ are each independently selected from the group consisting of $C_1$–$C_6$ alkyl, $C_3$–$C_6$ cycloalkyl, phenyl, biaryl, heteroaryl, or heterobiaryl, wherein the $C_1$–$C_6$ alky$_1$, $C_1$–$C_6$ cycloalkyl, phenyl, biaryl, hereroaryl, and heterobiaryl groups are unsubstituted or substituted with halogen, OH, $C_1$–$C_4$ alkyl, or $C_1$–$C_4$ haloalkyl, or when $R_3$ represents $NR_{11}R_{12}$, $R_{11}$ and $R_{12}$ may be taken together to form an optionally substituted $C_3$–$C_6$ aliphatic or $C_3$–$C_6$ aromatic heterocyclic ring.

9. A method according to claim 8 wherein the particles are polymeric beads.

10. A method according to claim 8 wherein at least one of the fluorescent labels is a compound of the formula:

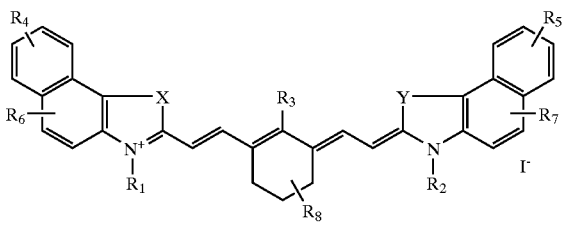

wherein:
  $R_4$, $R_5$, $R_6$, and $R_7$ are each independently selected from the group consisting of hydrogen, halogen, OH, $C_1$–$C_4$ alkyl, or $C_1$–$C_4$ haloalkyl, phenyl, and heteroaryl.

11. A method according to claim 8 wherein in at least one of the fluorescent labels, $R_1$ and $R_2$ are identical.

12. A method according to claim 8 wherein at least one of the fluorescent labels is a compound of the formula:

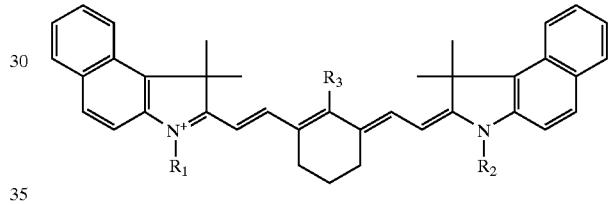

wherein:
  $R_1$ and $R_2$ are each independently a $C_1$–$C_{20}$ alkyl; and
  $R_3$ is H, halogen, or —S—phenyl.

13. A method according to claim 8 wherein in at least one of the fluorescent labels, the ring structures represented by A and B are each independently a benzoindole ring.

14. A method according to claim 8 wherein at least one of the fluorescent labels has a near-infrared excitation wavelength.

15. A method according to claim 8 wherein at least one of the fluorescent labels has an emitting light greater than 750 nm.

16. A particle comprising a fluorescent label of the formula:

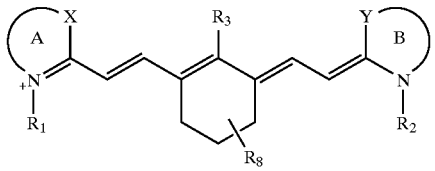

wherein:
  A and B each independently represent ring structures with sufficient carbon atoms to make up a cyanine nuclei;
  X and Y are each independently selected from the group consisting of O, S, $NR_9$, and $CR_9R_{10}$;
  $R_1$ and $R_2$ are each independently selected from the group consisting of H, $C_1$–$C_{20}$ alkyl, $C_1$–$C_{20}$ haloalkyl, $C_1$–$C_{20}$ alkylene, and $C_1$–$C_{20}$ haloalkylene;

$R_3$ is selected from the group consisting of H, halogen, OH, $OR_{11}$, $SR_{11}$, $NR_{11}R_{12}$ $C_1$–$C_6$ alkyl, $C_1$–$C_6$ alkylene, $C_3$–$C_6$ cycloalkyl, $C_3$–$C_6$ cycloheteroalkyl, $C_3$–$C_6$ cycloalkylene, $C_3$–$C_6$ cycloheteroalkylene, phenyl, biaryl, heteroaxyl, and heterobiaryl, wherein the $C_1$–$C_6$ alkyl, $C_1$–$C_6$ alkylene, $C_3$–$C_6$ cycloalkyl, $C_3$–$C_6$ cycloheteroalkyl, $C_3$–$C_6$ cycloalkylene, $C_3$–$C_6$ cycloheteroalkylene, phenyl, biaryl, heteroaryl and heterobiaryl groups are unsubstituted or substituted with halogen, OH, $C_1$–$C_4$ alkyl, or $C_1$–$C_4$ haloalkyl;

$R_6$ is selected from the group consisting of $C_1$–$C_4$ alkyl, and $C_1$–$C_4$ haloalkyl;

$R_9$ and $R_{10}$ are each independently selected from the group consisting of hydrogen, $C_1$–$C_4$ alkyl, and $C_1$–$C_4$ haloalkyl; and $R_{11}$ and $R_{12}$ are each independently selected from the group consisting of $C_1$–$C_6$ alkyl, $C_3$–$C_6$ cycloalkyl, phenyl, biaryl, heteroaryl, or heterobiaryl, wherein the $C_1$–$C_6$ alky$_1$, $C_1$–$C_6$ cycloalkyl, phenyl, biaryl, heteroaryl, and heterobiaryl groups are unsubstituted or substituted with halogen, OH, $C_1$–$C_4$ alkyl, or $C_1$–$C_4$ haloalkyl, or when $R_3$ represents $NR_{11}R_{12}$, $R_{11}$ and $R_{12}$ may be taken together to form an optionally substituted $C_3$–$C_6$ aliphatic or $C_3$–$C_6$ aromatic heterocyclic ring.

17. A particle according to claim 16 wherein the fluorescent labels are embedded within the particle.

18. A particle according to claim 16 wherein the fluorescent label is capable of emitting light at a maximum wavelength greater than 750 nm.

19. A particle according to claim 16 wherein the particle comprises two or more than two fluorescent labels in a first combination of relative amounts, the fluorescent labels being capable of being excited by light of a same excitation wavelength and capable of emitting lights at maximum wavelengths, distinguishable from each other, respectively.

20. A particle according to claim 19 wherein the fluorescent labels both have emitting lights greater than 750 nm.

21. A particle according to claim 19 wherein the excitation wavelength is about 780 nm.

22. A particle according to claim 19 wherein the fluorescent labels both have emitting lights greater than 750 nm and the maximum wavelengths of the emitting lights of the fluorescent labels differs by at least 20 nm.

23. A particle prepared by a process comprising:

a) preparing a particle suspension; and b) adding a solution of two or more fluorescent labels to the suspension, thereby incorporating the fluorescent labels into the particle, where at least one fluorescent label is a compound of the formula:

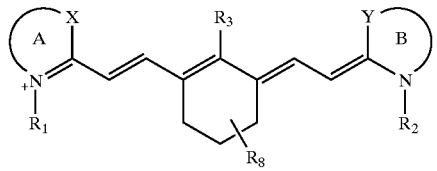

wherein:

A and B each independently represent ring structures with sufficient carbon atoms to make up a cyanine nuclei;

X and Y are each independently selected from the group consisting of O, S, $NR_9$, and $CR_9R_{10}$;

$R_1$ and $R_2$ are each independently selected from the group consisting of H, $C_1$–$C_{20}$ alkyl, $C_1$–$C_{20}$ haloalkyl, $C_1$–$C_{20}$ alkylene, and $C_1$–$C_{20}$ haloalkylene;

$R_3$ is selected from the group consisting of H, halogen, OH, $OR_{11}$, $SR_{11}$, $NR_{11}R_{12}$, $C_1$–$C_6$ alkyl, $C_1$–$C_6$ alkylene, $C_3$–$C_6$ cycloalkyl, $C_3$–$C_6$ cycloheteroalkyl, $C_3$–$C_6$ cycloalkylene, $C_3$–$C_6$ cycloheteroalkylene, phenyl, biaryl, heteroaryl, and heterobiaryl, wherein the $C_1$–$C_6$ alkyl, $C_1$–$C_6$ alkylene, $C_3$–$C_6$ cycloalkyl, $C_3$–$C_6$ cycloheteroalkyl, $C_3$–$C_6$ cycloalkylene, $C_3$–$C_6$ cycloheteroalkylene, phenyl, biaryl, heteroaryl and heterobiaryl groups are unsubstituted or substituted with halogen, OH, $C_1$–$C_4$ alkyl, or $C_1$–$C_4$ haloalkyl;

$R_8$ is selected from the group consisting of $C_1$–$C_4$ alkyl, and $C_1$–$C_4$ haloalkyl;

$R_9$ and $R_{10}$ are each independently selected from the group consisting of hydrogen, $C_1$–$C_4$ alkyl, and $C_1$–$C_4$ haloalkyl; and $R_{11}$ and $R_{12}$ are each independently selected from the group consisting of $C_1$–$C_6$ alkyl, $C_3$–$C_6$ cycloalkyl, phenyl, biaryl, heteroaryl, or heterobiaryl, wherein the $C_1$–$C_6$ alky$_1$, $C_1$–$C_6$ cycloalkyl, phenyl, biaryl, heteroaryl, and heterobiaryl groups are unsubstituted or substituted with halogen, OH, $C_1$–$C_4$ alkyl, or $C_1$–$C_4$ haloalkyl, or when $R_3$ represents $NR_{11}R_{12}$, $R_{11}$ and $R_{12}$ may be taken together to form an optionally substituted $C_3$–$C_6$ aliphatic or $C_3$–$C_6$ aromatic heterocyclic ring.

24. A particle prepared by a process according to claim 23 wherein the particle is a polymeric bead.

* * * * *